US011633112B2

(12) United States Patent
Stadler et al.

(10) Patent No.: US 11,633,112 B2
(45) Date of Patent: Apr. 25, 2023

(54) AUTOMATIC ALERT CONTROL FOR ACUTE HEALTH EVENT

(71) Applicant: Medtronic, Inc., Minneapolis, MN (US)

(72) Inventors: Robert W. Stadler, Shoreview, MN (US); Ryan D. Wyszynski, Oak Grove, MN (US); Paul J. DeGroot, Minneapolis, MN (US); Shantanu Sarkar, Roseville, MN (US); Paul G. Krause, Mahtomedi, MN (US); Kevin T. Ousdigian, Shoreview, MN (US); Grant A. Neitzell, Plymouth, MN (US); Christopher D. Koch, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/246,269

(22) Filed: Apr. 30, 2021

(65) Prior Publication Data
US 2022/0280047 A1 Sep. 8, 2022

Related U.S. Application Data

(60) Provisional application No. 63/158,189, filed on Mar. 8, 2021.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0004* (2013.01); *A61B 5/0024* (2013.01);
(Continued)

(58) Field of Classification Search
CPC ....... A61B 5/746; A61B 5/747; A61B 5/0004; A61B 5/0024; A61B 5/0204;
(Continued)

(56) References Cited

U.S. PATENT DOCUMENTS 5,416,695 A 5/1995 Stutman et al.
5,458,123 A 10/1995 Unger
(Continued)

FOREIGN PATENT DOCUMENTS

CA 3075015 A1 9/2021
CN 105068486 A 11/2015
(Continued)

OTHER PUBLICATIONS

Samani et al., "Robotic Automated External Defibrillator Ambulance for Emergency Medical Service in Smart Cities," IEEE Access, vol. 4., Jan. 2016, pp. 268-283.
(Continued)

*Primary Examiner* — Christopher A Flory
(74) *Attorney, Agent, or Firm* — Shumaker & Sieffert, P.A.

(57) ABSTRACT

An example device of a patient includes an antenna configured to wirelessly receive communication from a medical device; and processing circuitry coupled to the antenna and configured to: determine that the received communication indicates that a patient is experiencing an acute health event; in response to the determination, determine one or more physical states of the patient based on sensed data from one or more sensors; confirm that the patient is not experiencing the acute health event based on the determined one or more physical states; and output information based on the confirmation that the patient is not experiencing the acute health event.

33 Claims, 5 Drawing Sheets

(51) Int. Cl.
  *A61B 5/103* (2006.01)
  *A61B 5/145* (2006.01)
(52) U.S. Cl.
  CPC ........ *A61B 5/1032* (2013.01); *A61B 5/14542* (2013.01); *A61B 5/681* (2013.01); *A61B 5/6898* (2013.01); *A61B 5/746* (2013.01); *A61B 5/747* (2013.01); *A61B 2562/0219* (2013.01)
(58) Field of Classification Search
  CPC ... A61B 5/1032; A61B 5/14542; A61B 5/681; A61B 5/6898; A61B 2562/0219; G16H 40/60; G16H 40/63; G16H 40/67
  See application file for complete search history.

(56) References Cited

U.S. PATENT DOCUMENTS

| | | | |
|---|---|---|---|
| 5,944,680 | A | 8/1999 | Christopherson et al. |
| 6,292,687 | B1 | 9/2001 | Lowell et al. |
| 6,493,581 | B2 | 12/2002 | Russell |
| 6,609,023 | B1 | 8/2003 | Fischell et al. |
| 6,907,238 | B2 | 6/2005 | Leung |
| 6,980,112 | B2 | 12/2005 | Nee |
| 7,194,354 | B1 | 3/2007 | Oran et al. |
| 7,212,849 | B2 | 5/2007 | Zhang et al. |
| 7,312,709 | B2 | 12/2007 | Kingston |
| 7,353,179 | B2 | 4/2008 | Ott et al. |
| 7,396,330 | B2 | 7/2008 | Banet et al. |
| 7,480,529 | B2 | 1/2009 | Li |
| 7,502,498 | B2 | 3/2009 | Wen et al. |
| 7,558,623 | B2 | 7/2009 | Fischell et al. |
| 7,689,282 | B2 | 3/2010 | Zhang et al. |
| 7,702,382 | B2 | 4/2010 | Xue |
| 7,715,905 | B2 | 5/2010 | Kurzweil et al. |
| 7,733,224 | B2 | 6/2010 | Tran |
| 7,801,596 | B2 | 9/2010 | Fischell et al. |
| 7,840,277 | B2 | 11/2010 | Matos |
| 7,844,323 | B2 | 11/2010 | Fischell et al. |
| 7,860,559 | B2 | 12/2010 | Fischell et al. |
| 7,889,092 | B2 | 2/2011 | Volk et al. |
| 7,894,883 | B2 | 2/2011 | Gunderson et al. |
| 7,991,460 | B2 | 8/2011 | Fischell et al. |
| 8,073,536 | B2 | 12/2011 | Gunderson et al. |
| 8,073,537 | B2 | 12/2011 | Gunderson et al. |
| 8,108,036 | B2 | 1/2012 | Tran |
| 8,112,153 | B2 * | 2/2012 | Giftakis ............... A61B 5/4094 607/45 |
| 8,170,609 | B2 | 5/2012 | Hedtke et al. |
| 8,170,653 | B2 | 5/2012 | Fischell et al. |
| 8,204,580 | B2 | 6/2012 | Kurzweil |
| 8,214,043 | B2 | 7/2012 | Matos |
| 8,224,430 | B2 | 7/2012 | Fischell et al. |
| 8,239,020 | B2 | 8/2012 | Zhang et al. |
| 8,265,740 | B2 | 9/2012 | Fischell et al. |
| 8,265,751 | B2 | 9/2012 | Zhang et al. |
| 8,275,457 | B1 | 9/2012 | Fischell et al. |
| 8,301,236 | B2 | 10/2012 | Baumann et al. |
| 8,332,233 | B2 | 12/2012 | Ott |
| 8,352,018 | B2 | 1/2013 | Xue |
| 8,583,251 | B2 | 1/2013 | Matos |
| 8,401,644 | B2 | 3/2013 | Gunderson et al. |
| 8,423,128 | B2 | 4/2013 | Goto |
| 8,433,399 | B1 | 4/2013 | Nosrati et al. |
| 8,437,840 | B2 | 5/2013 | Patel et al. |
| 8,461,988 | B2 | 6/2013 | Tran |
| 8,473,065 | B2 | 6/2013 | Matos |
| 8,483,807 | B2 | 7/2013 | Kurzweil et al. |
| 8,512,257 | B2 | 8/2013 | Fischell et al. |
| 8,521,281 | B2 | 8/2013 | Patel et al. |
| 8,525,673 | B2 | 9/2013 | Tran |
| 8,525,687 | B2 | 9/2013 | Tran |
| 8,531,291 | B2 | 9/2013 | Tran |
| 8,562,524 | B2 | 10/2013 | Osorio |
| 8,565,882 | B2 | 10/2013 | Matos |
| 8,630,702 | B2 | 1/2014 | Fischell et al. |
| 8,680,991 | B2 | 3/2014 | Tran |
| 8,682,284 | B2 | 3/2014 | Brackett et al. |
| 8,684,922 | B2 | 4/2014 | Tran |
| 8,706,217 | B2 | 4/2014 | Bardy et al. |
| 8,706,225 | B2 | 4/2014 | Matos |
| 8,747,336 | B2 | 6/2014 | Tran |
| 8,774,909 | B2 | 7/2014 | Patel et al. |
| 8,805,529 | B2 | 8/2014 | Matos |
| 8,825,146 | B2 | 9/2014 | Li |
| 8,831,725 | B2 | 9/2014 | Gunderson et al. |
| 8,849,400 | B2 | 9/2014 | Gunderson et al. |
| 8,862,393 | B2 | 10/2014 | Zhou et al. |
| 8,886,296 | B2 | 11/2014 | Patel |
| 8,923,960 | B2 | 12/2014 | Goto |
| 8,954,137 | B2 | 2/2015 | Kurzweil et al. |
| 8,965,494 | B2 | 2/2015 | Fischell et al. |
| 8,983,587 | B2 | 3/2015 | Kurzweil et al. |
| 8,983,682 | B1 | 3/2015 | Peeters et al. |
| 9,082,156 | B2 | 7/2015 | Matos |
| 9,095,727 | B2 | 8/2015 | Matos |
| 9,101,278 | B2 | 8/2015 | Fischell et al. |
| 9,138,590 | B2 | 9/2015 | Zhang et al. |
| 9,179,255 | B2 | 11/2015 | Stephens et al. |
| 9,179,851 | B2 | 11/2015 | Baumann et al. |
| 9,204,796 | B2 | 12/2015 | Tran |
| 9,237,243 | B2 | 1/2016 | Jensen et al. |
| 9,241,677 | B2 | 1/2016 | Liao-Chen et al. |
| 9,254,092 | B2 | 2/2016 | Albert et al. |
| 9,293,025 | B2 | 3/2016 | Zhang |
| 9,307,383 | B1 | 4/2016 | Patrick |
| 9,351,640 | B2 | 5/2016 | Tran |
| 9,445,736 | B2 | 9/2016 | Kurzweil et al. |
| 9,456,787 | B2 | 10/2016 | Venkatraman et al. |
| 9,468,383 | B2 | 10/2016 | Fischell et al. |
| 9,491,277 | B2 | 11/2016 | Vincent |
| 9,498,152 | B2 | 11/2016 | Bowers |
| 9,642,167 | B1 | 5/2017 | Snyder et al. |
| 9,662,015 | B2 | 5/2017 | Proud et al. |
| 9,681,814 | B2 | 6/2017 | Galloway et al. |
| 9,724,008 | B2 | 8/2017 | Sullivan et al. |
| 9,735,896 | B2 | 8/2017 | Flippo et al. |
| 9,770,181 | B2 | 9/2017 | Kurzweil et al. |
| 9,775,520 | B2 | 10/2017 | Tran |
| 9,824,188 | B2 | 11/2017 | Brown et al. |
| 9,826,358 | B2 | 11/2017 | Ryan et al. |
| 9,852,599 | B1 * | 12/2017 | Slavin ................. G08B 21/043 |
| 9,855,434 | B2 | 1/2018 | Matos |
| 9,901,252 | B2 | 2/2018 | Tran |
| 9,913,583 | B2 | 3/2018 | Smith, Sr. |
| 9,979,810 | B2 | 5/2018 | Mazar et al. |
| 9,997,055 | B2 | 6/2018 | Ball |
| 10,003,394 | B2 | 6/2018 | Bromberg et al. |
| 10,039,469 | B2 | 8/2018 | Higgins et al. |
| 10,044,857 | B2 | 8/2018 | Philbin |
| 10,085,115 | B2 | 9/2018 | Mayor et al. |
| 10,117,606 | B2 * | 11/2018 | Feldman ............ A61B 5/14865 |
| 10,123,741 | B2 | 11/2018 | Wang et al. |
| 10,136,826 | B2 | 11/2018 | Sullivan et al. |
| 10,165,400 | B2 | 12/2018 | Raj |
| 10,201,710 | B2 | 2/2019 | Jackson et al. |
| 10,272,010 | B2 | 4/2019 | Freeman et al. |
| 10,278,050 | B2 | 4/2019 | Winkler et al. |
| 10,307,060 | B2 | 6/2019 | Tran |
| 10,362,940 | B2 | 7/2019 | Tran |
| 10,368,807 | B2 | 8/2019 | Melker et al. |
| 10,375,558 | B2 | 8/2019 | Katz et al. |
| 10,463,295 | B2 | 11/2019 | Zhou |
| 10,492,686 | B2 | 12/2019 | Hunter et al. |
| 10,517,479 | B2 | 12/2019 | Tran |
| 10,531,266 | B2 | 1/2020 | Rauner et al. |
| 10,540,878 | B2 | 1/2020 | Hunter et al. |
| 10,602,942 | B2 | 3/2020 | Shakur et al. |
| 10,616,664 | B2 | 4/2020 | Alman et al. |
| 10,616,747 | B2 | 4/2020 | Piett et al. |
| 10,617,356 | B2 | 4/2020 | Wang et al. |
| 10,624,550 | B2 | 4/2020 | Soli et al. |
| 10,657,796 | B2 | 5/2020 | Bowers |
| 10,674,342 | B2 | 6/2020 | Park et al. |

(56) References Cited

U.S. PATENT DOCUMENTS

| | | |
|---|---|---|
| 10,758,140 B2 | 9/2020 | Kurzweil et al. |
| 10,814,978 B2 | 10/2020 | Walker et al. |
| 10,882,180 B2 | 1/2021 | Wright et al. |
| 10,888,705 B2 | 1/2021 | Matos |
| 10,981,009 B2 | 4/2021 | Jackson et al. |
| 11,024,432 B2 | 6/2021 | Chiu et al. |
| 11,064,339 B2 | 7/2021 | Harare et al. |
| 11,103,176 B2 | 8/2021 | Gallowav et al. |
| 11,103,194 B2 | 8/2021 | Galloway et al. |
| 11,160,484 B2 | 11/2021 | Sullivan et al. |
| 1,120,217 A1 | 12/2021 | Klinkner et al. |
| 11,198,017 B2 | 12/2021 | Kaib et al. |
| 11,218,584 B2 | 1/2022 | Martin et al. |
| 11,219,373 B2 | 1/2022 | Eggers et al. |
| 11,228,891 B2 | 1/2022 | King-Berkman et al. |
| 11,230,242 B2 | 1/2022 | Makled et al. |
| 11,234,604 B2 | 2/2022 | Albert |
| 11,278,201 B2 | 3/2022 | Thomson et al. |
| 11,311,230 B2 | 4/2022 | Sullivan et al. |
| 11,341,839 B2 | 5/2022 | Cruver et al. |
| 11,344,244 B2 | 5/2022 | Albert |
| 11,363,952 B2 | 6/2022 | Venkatraman et al. |
| 2003/0023175 A1 | 1/2003 | Arzbaecher et al. |
| 2003/0176798 A1 | 9/2003 | Simon |
| 2003/0191402 A1* | 10/2003 | Arzbaecher .......... A61B 5/0006 600/509 |
| 2003/0214409 A1* | 11/2003 | Hickle .................. A61B 5/746 340/573.1 |
| 2003/0233129 A1* | 12/2003 | Matos ................ A61N 1/39044 607/5 |
| 2004/0172069 A1 | 9/2004 | Hakala |
| 2004/0199212 A1 | 10/2004 | Fischell et al. |
| 2005/0065445 A1* | 3/2005 | Arzbaecher .......... A61B 5/0006 600/509 |
| 2005/0154325 A1 | 7/2005 | Lauter et al. |
| 2005/0228305 A1 | 10/2005 | Nagata et al. |
| 2006/0030781 A1 | 2/2006 | Shennib |
| 2006/0155206 A1 | 7/2006 | Lynn |
| 2006/0173498 A1 | 8/2006 | Banville et al. |
| 2006/0284732 A1 | 12/2006 | Brock-Fisher |
| 2007/0043585 A1* | 2/2007 | Matos ................... G16H 40/67 705/2 |
| 2007/0249944 A1 | 10/2007 | Fischell et al. |
| 2007/0260285 A1 | 11/2007 | Libbus et al. |
| 2007/0260289 A1* | 11/2007 | Giftakis .............. A61B 5/4094 607/45 |
| 2007/0293775 A1 | 12/2007 | Fischell et al. |
| 2007/0299473 A1* | 12/2007 | Matos ................... A61N 1/3904 607/9 |
| 2008/0058660 A1 | 3/2008 | Fischell et al. |
| 2008/0064973 A1 | 3/2008 | Fischell et al. |
| 2008/0139954 A1 | 6/2008 | Day et al. |
| 2008/0177194 A1 | 7/2008 | Zhang et al. |
| 2008/0270036 A1 | 10/2008 | Webb |
| 2009/0054027 A1 | 2/2009 | Jenkins |
| 2009/0240156 A1* | 9/2009 | Fischell ................ A61B 5/287 600/509 |
| 2009/0322513 A1 | 12/2009 | Hwang et al. |
| 2009/0326595 A1* | 12/2009 | Brockway ............. G16H 20/40 607/3 |
| 2010/0016746 A1 | 1/2010 | Hampton et al. |
| 2010/0022902 A1 | 1/2010 | Lee et al. |
| 2011/0054934 A1 | 3/2011 | Vesto |
| 2011/0112417 A1 | 5/2011 | Gunderson et al. |
| 2011/0193704 A1* | 8/2011 | Harper ................... A61B 5/14 340/573.1 |
| 2011/0288417 A1 | 11/2011 | Pinter et al. |
| 2012/0190969 A1* | 7/2012 | Kameli ............. A61N 1/39624 607/29 |
| 2012/0191150 A1* | 7/2012 | Kameli ................ A61N 1/3787 607/4 |
| 2012/0191151 A1* | 7/2012 | Kameli ................ A61N 1/378 607/6 |
| 2012/0191152 A1* | 7/2012 | Kameli ................ A61N 1/375 607/7 |
| 2012/0220835 A1 | 8/2012 | Chung |
| 2012/0242501 A1 | 9/2012 | Tran et al. |
| 2012/0330171 A1 | 12/2012 | Zhang et al. |
| 2013/0095459 A1 | 4/2013 | Tran |
| 2013/0211291 A1 | 8/2013 | Tran |
| 2013/0245466 A1 | 9/2013 | Sachanandani et al. |
| 2014/0100497 A1 | 4/2014 | Hayashi et al. |
| 2014/0152436 A1 | 6/2014 | Langer |
| 2014/0163425 A1 | 6/2014 | Tran |
| 2014/0213202 A1* | 7/2014 | Wang ...................... H03B 5/326 455/125 |
| 2014/0293053 A1* | 10/2014 | Chuang ................ A61B 5/117 348/148 |
| 2015/0018658 A1 | 1/2015 | Fischell et al. |
| 2015/0112605 A1* | 4/2015 | Watson ................ A61B 5/7221 702/19 |
| 2015/0158988 A1 | 6/2015 | Sawaki et al. |
| 2015/0173689 A1 | 6/2015 | Owen et al. |
| 2015/0223759 A1 | 8/2015 | Ong et al. |
| 2015/0302539 A1* | 10/2015 | Mazar .................... G16H 40/20 705/3 |
| 2015/0366518 A1 | 12/2015 | Sampson |
| 2016/0008614 A1 | 1/2016 | Zhang et al. |
| 2016/0035204 A1 | 2/2016 | Jansen |
| 2016/0120434 A1 | 5/2016 | Park et al. |
| 2016/0128595 A1 | 5/2016 | Fischell et al. |
| 2016/0135706 A1 | 5/2016 | Sullivan et al. |
| 2016/0151021 A1 | 6/2016 | Feng et al. |
| 2016/0174875 A1 | 6/2016 | Forster et al. |
| 2016/0328950 A1 | 11/2016 | Pelletier et al. |
| 2016/0331330 A1 | 11/2016 | Freeman et al. |
| 2017/0007167 A1 | 1/2017 | Kostic et al. |
| 2017/0083667 A1 | 3/2017 | Darrah et al. |
| 2017/0246329 A1 | 8/2017 | Lloyd |
| 2017/0281097 A1 | 10/2017 | Thakur et al. |
| 2017/0296076 A1 | 10/2017 | Mahajan et al. |
| 2017/0330438 A1 | 11/2017 | Howard et al. |
| 2017/0366921 A1 | 12/2017 | Pflugh et al. |
| 2018/0008159 A1 | 1/2018 | Wang |
| 2018/0091657 A1 | 3/2018 | Brown et al. |
| 2018/0113986 A1 | 4/2018 | Zhu |
| 2018/0113987 A1 | 4/2018 | Zhu |
| 2018/0116537 A1 | 5/2018 | Sullivan et al. |
| 2018/0117299 A1 | 5/2018 | Gustavson et al. |
| 2018/0146922 A1 | 5/2018 | Wang et al. |
| 2018/0192894 A1 | 7/2018 | An et al. |
| 2018/0221645 A1 | 8/2018 | Medema et al. |
| 2018/0235537 A1* | 8/2018 | Whiting ............ A61N 1/36564 |
| 2018/0260706 A1 | 9/2018 | Galloway et al. |
| 2018/0301017 A1 | 10/2018 | Dizengof et al. |
| 2018/0322405 A1 | 11/2018 | Fadell et al. |
| 2018/0338731 A1 | 11/2018 | Addison et al. |
| 2018/0348759 A1* | 12/2018 | Freeman .............. A61N 1/3904 |
| 2019/0043616 A1 | 2/2019 | Howard et al. |
| 2019/0066538 A1 | 2/2019 | Chao et al. |
| 2019/0125273 A1 | 5/2019 | Sharma et al. |
| 2019/0275225 A1 | 9/2019 | Brown |
| 2019/0279480 A1* | 9/2019 | Lee ...................... A61B 5/746 |
| 2019/0290216 A1* | 9/2019 | Koyama ................ A61B 5/01 |
| 2019/0307328 A1 | 10/2019 | Tran |
| 2019/0336767 A1* | 11/2019 | Klepfer ............. A61M 60/148 |
| 2019/0365264 A1 | 12/2019 | Freeman et al. |
| 2019/0365269 A1 | 12/2019 | Jun |
| 2019/0391581 A1 | 12/2019 | Vardaro et al. |
| 2020/0008696 A1 | 1/2020 | Sirendi et al. |
| 2020/0038671 A1 | 2/2020 | Schulhauser et al. |
| 2020/0069245 A1 | 3/2020 | Zhou |
| 2020/0077892 A1 | 3/2020 | Tran |
| 2020/0085380 A1 | 3/2020 | Sampson |
| 2020/0100693 A1* | 4/2020 | Velo ...................... A61B 5/486 |
| 2020/0146550 A1* | 5/2020 | Tunnell ................ A61B 5/0022 |
| 2020/0160991 A1 | 5/2020 | Smith et al. |
| 2020/0305737 A1 | 10/2020 | Tseng et al. |
| 2020/0337581 A1 | 10/2020 | Jung et al. |
| 2020/0342966 A1 | 10/2020 | Stern et al. |
| 2020/0352462 A1 | 11/2020 | Pedalty et al. |
| 2020/0352466 A1 | 11/2020 | Chakravarthy et al. |

(56) References Cited

U.S. PATENT DOCUMENTS

| | | |
|---|---|---|
| 2020/0352522 A1 | 11/2020 | Chakravarthy et al. |
| 2020/0357519 A1 | 11/2020 | Chakravarthy et al. |
| 2020/0373005 A1 | 11/2020 | Halsne et al. |
| 2021/0118562 A1 | 4/2021 | Matos |
| 2021/0121090 A1 | 4/2021 | Weinstein et al. |
| 2021/0138254 A1 | 5/2021 | Matos |
| 2021/0154487 A1 | 5/2021 | Bongberg et al. |
| 2021/0169392 A1 | 6/2021 | Albert et al. |
| 2021/0186329 A1 | 6/2021 | Tran |
| 2021/0259560 A1 | 8/2021 | Venkatraman et al. |
| 2021/0314756 A1 | 10/2021 | Brooks et al. |
| 2021/0338134 A1 | 11/2021 | Chakravarthy et al. |
| 2021/0338138 A1 | 11/2021 | Pedalty et al. |
| 2021/0343132 A1 | 11/2021 | Bonser |
| 2021/0343416 A1 | 11/2021 | Chakravarthy et al. |
| 2021/0345934 A1 | 11/2021 | Landgraf et al. |
| 2021/0353166 A1 | 11/2021 | Sirendi et al. |
| 2021/0401349 A1 | 12/2021 | Schram |
| 2022/0039729 A1 | 2/2022 | Fontanarava et al. |
| 2022/0051548 A1 | 2/2022 | Pellegrini et al. |
| 2022/0095982 A1 | 3/2022 | de Saint Victor et al. |
| 2022/0183607 A1 | 6/2022 | Volosin et al. |
| 2022/0218259 A1 | 7/2022 | Laversin et al. |

FOREIGN PATENT DOCUMENTS

| | | | | |
|---|---|---|---|---|
| CN | 106562777 | A | 4/2017 | |
| CN | 207924885 | U | 9/2018 | |
| CN | 208460154 | U | 2/2019 | |
| CN | 109820492 | A | 5/2019 | |
| CN | 217014071 | U | 7/2022 | |
| EP | 2689363 | A2 | 1/2014 | |
| GB | 2569157 | A * | 6/2019 | ........... A61B 5/0031 |
| GB | 2590556 | B | 6/2021 | |
| GB | 2600710 | A | 5/2022 | |
| KR | 20030008655 | A | 1/2003 | |
| KR | 100637566 | B1 | 10/2006 | |
| KR | 101756787 | B1 | 7/2017 | |
| MX | 2016007079 | A | 11/2017 | |
| WO | WO 2005021089 | A1 | 3/2005 | |
| WO | 2010105053 | A3 | 1/2011 | |
| WO | 2017059274 | A1 | 4/2017 | |
| WO | 2019096876 | A1 | 5/2019 | |
| WO | 2019110963 | A1 | 6/2019 | |
| WO | 2020115747 | A1 | 6/2020 | |
| WO | 2020226879 | | 11/2020 | |
| WO | 2020226881 | | 11/2020 | |
| WO | 2020226887 | | 11/2020 | |
| WO | 2021084535 | | 5/2021 | |
| WO | 2021133360 | A1 | 7/2021 | |
| WO | 2022034045 | | 2/2022 | |
| WO | 2022034480 | | 2/2022 | |
| WO | 2022070109 | | 4/2022 | |
| WO | 2022130152 | | 6/2022 | |

OTHER PUBLICATIONS

Roberts, "Best Buy Makes Deal to Provide its Senior Services on Apple Watch," Star Tribune, Mar. 3, 2021, 2pp.

Chan et al., "Contactless Cardiac Arrest Detection Using Smart Devices," NPJ Digital Medicine, vol. 2, No. 52, Jun. 19, 2019, 8 pp.

Bayanbay et al., "The Use of Unmanned Aerial Vehicle for Emergency Medical Assistance," 2019 20th International Conference of Young Specialists on Micro/Nanotechnologies and Electron Devices (EDM), Jun. 29-Jul. 3, 2019, pp. 597-600.

"Highlights of the 2020 American Heart Association Guidelines for CPR and ECC," American Heart Association, 2020 (Applicant points out, in accordance with MPEP 609.04(a), that the year of publication, 2020, is sufficiently earlier than the effective U.S. filing date, so that the particular month of publication is not in issue.) 32 p.

Solomon et al., "Sudden Death in Patients with Myocardial Infarction and Left Ventricular Dysfunction, Heart Failure, or Both," vol. 352, No. 25, Jun. 23, 2005, pp. 2581-2588.

Shcherbina et al., "Accuracy in Wrist-Worn, Sensor-Based Measurements of Heart Rate and Energy Expenditure in a Diverse Cohort," Journal of Personalized Medicine, vol. 3, No. 7, May 24, 2017, 12 pp.

Wang et al., "Accuracy of Wrist-Worn Heart Rate Monitors," JAMA Cardiology, vol. 2, No. 1, Jan. 2017, pp. 104-106.

Seshadri et al., "Accuracy of Apple Watch for Detection of Atrial Fibrillation," Circulation, vol. 141, No. 8, Feb. 25, 2020, pp. 702-703.

Tarakji et al., "Using a Novel Wireless System for Monitoring Patients After the Atrial Fibrillation Ablation Procedure: The iTransmit Study," Heart Rhythm Journal, vol. 12, No. 3, Mar. 1, 2015, pp. 554-559.

Instructions for Irregular Rhythm Notification, Apple Inc., Jun. 2020, 154 pp.

Perez et al., "Large-Scale Assessment of a Smartwatch to Identify Atrial Fibrillation," The New England Journal of Medicine, vol. 381, No. 20, Nov. 14, 2019, pp. 1909-1917.

Burke et al., "Smartwatch Detection of Ventricular Tachycardia: Case Series," Heart Rhythm Case Reports, vol. 6, No. 10, Oct. 2020, pp. 801-804.

Ringwald et al., "Smart Watch Recording of Ventricular Tachycardia: Case Study," American Journal of Emergency Medicine, vol. 38, No. 4, Apr. 1, 2020, pp. 849.e3-849.e5.

"Using Apple Watch for Arrhythmia Detection," Apple, Inc., Dec. 2020, 17 pp.

Auer et al., "A Smartwatch to Identify Atrial Fibrillation," The New England Journal of Medicine, vol. 382, No. 10, Mar. 5, 2020, pp. 974-976.

Singh, "Detecting Atrial Fibrillation with with the Apple Watch: Our Clinically Validated Results," https://blog.cardiogr.am/detecting-atrial-fibrillation-with-the-apple-watch-our-clinically-validated-results-ea66163e0fa6, Mar. 21, 2018, 14 pp.

Campion et al., "Watched by Apple," The New England Journal of Medicine, vol. 381, No. 20, Nov. 14, 2019, pp. 1964-1965.

Hwang et al., "Assessing Accuracy of Wrist-Worn Wearable Devices in Measurement of Paroxysmal Supraventricular Tachycardia Heart Rate," Korean Circulation Journal, vol. 49, No. 5, May 2019, pp. 437-445.

Blomberg et al., "Effect of Machine Learning on Dispatcher Recognition of Out-of-Hospital Cardiac Arrest During Calls to Emergency Medical Services A Randomized Clinical Trial," JAMA Network Open, Jan. 6, 2021, 10 pp.

Book of Abstracts, Acta Cardiologica, vol. 76, supp 1, Feb. 22, 2021, 52 pp.

"Cardiac Arrest: An Important Public Health Issue," CDC, retrieved from https://www.cdc.gov/dhdsp/docs/cardiac-arrest-infographic.pdf, on Apr. 23, 2021, 2 pp.

Cares Annual Report 2019, 2019 (Applicant points out, in accordance with MPEP 609.04(a), that the year of publication, 2019, is sufficiently earlier than the effective U.S. filing date, so that the particular month of publication is not in issue.) 48 pp.

Okubo et al., "Characteristics of Paediatric Out-of-Hospital Cardiac Arrest in the United States," Resuscitation, vol. 153, Apr. 27, 2020, pp. 227-233.

"Heart Disease and Stroke Statistics—2019 Update A Report From the American Heart Association," Circulation, vol. 139, Mar. 5, 2019 pp. e56-e528.

Than et al., "Machine Learning to Predict the Likelihood of Acute Myocardial Infarction," Circulation, vol. 140, Sep. 10, 2019, pp. 899-909.

Li et al., "The Current State of Mobile Phone Apps for Monitoring Heart Rate, Heart Rate Variability, and Atrial Fibrillation: Narrative Review," JMIR Mhealth Uhealth, vol. 7, No. 2, e11606, Feb. 15, 2019, 16 pp.

Mell et al., "Emergency Medical Services Response Times in Rural, Suburban, and Urban Areas," JAMA Surgery, vol. 152, No. 10, Oct. 2017, pp. 983-984.

Deo et al., "Epidemiology and Genetics of Sudden Cardiac Death," Circulation, vol. 125, No. 4, Jan. 31, 2012, pp. 620-637.

(56) References Cited

OTHER PUBLICATIONS

Rudner et al., "Interrogation of Patient Smartphone Activity Tracker to Assist Arrhythmia Management," Annals of Emergency Medicine, vol. 68, No. 3, Sep. 2016, pp. 292-294.
Goldberger et al., "Risk Stratification for Sudden Cardiac Death A Plan for the Future," Circulation, vol. 129, No. 4, Jan. 28, 2014, pp. 516-526.
Hirano et al., "Early Outcome Prediction for Out-Of-Hospital Cardiac Arrest with Initial Shockable Rhythm Using Machine Learning Models," Resuscitation, vol. 158, No. 145, Jan. 2021, pp. 49-56.
"Monitor your heart rate with Apple Watch," retrieved from https://support.apple.com/en-us/HT204666, on Apr. 23, 2021, 8 pp.
Sudden Cardiac Arrest Meeting the Challenge, The Joint Commission, 2011 (Applicant points out, in accordance with MPEP 609.04(a), that the year of publication, 2011, is sufficiently earlier than the effective U.S. filing date, so that the particular month of publication is not in issue.) 87 pp.
Bumgarner et al., "Smartwatch Algorithm for Automated Detection of Atrial Fibrillation," Journal of the American College of Cardiology, vol. 71, No. 21, May 29, 2018, pp. 2381-2388.
"Protocol 9, Cardiac or Respiratory Arrest," The EMD Protocol, National Academy Medical Priioty Dispatch System, Accessed on Apr. 23, 2021, 5 pp.
Turakhia et al., "Rationale and Design of a Large-Scale, App-Based Study to Identify Cardiac Arrhythmias Using a Smartwatch: The Apple Heart Study," American Heart Journal, vol. 207, Jan. 2019, pp. 66-75.
Salcido et al., "Have Outcomes After Out of Hospital Cardiac Arrest Improved Over Time?," Circulation: Cardiovascular Quality and Outcomes, vol. 14, No. 3, e007752, Mar. 2021, pp. 290-291.
Zaman et al., "Sudden Cardiac Death Early After Myocardial Infarction Pathogenesis, Risk Stratification, and Primary Prevention," Circulation, vol. 129, No. 23, Jun. 10, 2014, pp. 2426-2435.
Papini et al., "Wearable Monitoring of Sleep-Disordered Breathing: Estimation of the Apnea-Hypopnea Index Using Wrist-Worn Reflective Photoplethysmography," Scientific Reports, vol. 10, No. 13512, Aug. 11, 2020, 15 pp.
Giancaterino et al., "The Smartwatch Will See You Now: Implications of Mass Screening for Atrial Fibrillation," Journal of the American College of Cardiology, vol. 72, No. 12, Sep. 18, 2018, pp. 1433-1434.
Carpenter et al., "Smart-Watches: a Potential Challenger to the Implantable Loop Recorder?," Europace, vol. 18, Feb. 2016, pp. 791-793.
Koshy et al., "Smart Watches for Heart Rate Assessment in Atrial Arrhythmias," International Journal of Cardiology, vol. 266, Sep. 1, 2018, pp. 124-127.
Medtronic Ling II, Medtronic CareLink Network, Jan. 29, 2021, 11 pp.
Waldmann et al., "Temporal Trends of Out-of-Hospital Cardiac Arrests Without Resuscitation Attempt by Emergency Medical Services," Circulation: Cardiovascular Quality and Outcomes, vol. 14, No. e006626, Mar. 2021, pp. 279-289.
Beauchamp et al., "The Use of Wearables in Clinical Trials During Cancer Treatment: Systematic Review," JMIR Mhealth Uhealth, vol. 8, No. 11, e22006, Nov. 2020, 15 pp.
Singhal et al., "The Role of Wearables in Heart Failure," Current Heart Failure Reports, vol. 17, No. 4, Jun. 3, 2020, pp. 125-132.
Samsung Galaxy Watch3 LTE Smartwatch, retrieved from https://www.samsung.com/us/watches/galaxy-watch3/#health, on Apr. 29, 2021, 31 pp.
U.S. Appl. No. 16/593,739, filed Oct. 4, 2019, by Haddad et al.
U.S. Appl. No. 17/101,945, filed Nov. 23, 2020, by Anderson et al.
U.S. Appl. No. 17/301,923, filed Apr. 19, 2021, by Anderson et al.
U.S. Appl. No. 17/006,444, filed Aug. 28, 2020, by Schulhauser.
Dayananda et al., "An Interconnected Architecture for an Emergency Medical Response Unmanned Aerial System," 2017 IEEE/AIAA 36th Digital Avionics Systems Conference (DASC), Sep. 17-21, 2017, pp. 1-6.
U.S. Appl. No. 17/383,170, filed Jul. 22, 2021, naming inventors Haddad et al.
U.S. Appl. No. 17/459,713, filed Aug. 27, 2021, naming inventors Schulhauser et al.
U.S. Appl. No. 63/158,189, by Medtronic, Inc., filed Mar. 8, 2021.
International Search Report and Written Opinion of International Application No. PCT/US2022/016503, dated May 5, 2022, 7 pp.

\* cited by examiner

AUTOMATIC ALERT CONTROL FOR ACUTE HEALTH EVENT

FIELD

This disclosure generally relates to systems including medical devices and, more particularly, to monitoring of patient health using such systems.

BACKGROUND

A variety of devices are configured to monitor physiological signals of a patient. Such devices include implantable or wearable medical devices, as well as a variety of wearable health or fitness tracking devices. The physiological signals sensed by such devices include as examples, electrocardiogram (ECG) signals, respiration signals, perfusion signals, activity and/or posture signals, pressure signals, blood oxygen saturation signals, body composition, and blood glucose or other blood constituent signals. In general, using these signals, such devices facilitate monitoring and evaluating patient health over a number of months or years, outside of a clinic setting.

In some cases, such devices are configured to detect acute health events based on the physiological signals, such as episodes of cardiac arrhythmia, myocardial infarction, stroke, or seizure. Example arrhythmia types include cardiac arrest (e.g., asystole), ventricular tachycardia (VT), pulseless electrical activity (PEA), and ventricular fibrillation (VF). The devices may store ECG and other physiological signal data collected during a time period including an episode as episode data. Such acute health events are associated with significant rates of death, particularly if not treated quickly.

For example, VF and other malignant tachyarrhythmias are the most commonly identified arrhythmia in sudden cardiac arrest (SCA) patients. If this arrhythmia continues for more than a few seconds, it may result in cardiogenic shock and cessation of effective blood circulation. The survival rate from SCA decreases between 7 and 10 percent for every minute that the patient waits for defibrillation. Consequently, sudden cardiac death (SCD) may result in a matter of minutes.

SUMMARY

In general, the disclosure describes techniques for controlling the delivery of an alert based on confirmation, with a computing device of a patient, of whether the patient is experiencing an acute health event. The patient "experiencing" the acute health event includes examples where the patient is currently experiencing the acute health event, examples where the acute health event is imminent, and examples where there is a suprathreshold likelihood of experiencing the event within a particular timeframe. An implantable medical device (IMD), such as an insertable loop recorder (ILR), may be configured to detect the possibility of the acute health event. In response, the IMD may cause output of an alert to trigger medical response. However, there may be instances where the alert should be ceased, prevented, or delayed. For instance, in some examples, the patient may recover from the acute health event without emergency medical intervention. As another example, the detection of the acute health event may be incorrect (e.g., false positive).

In one or more examples, a computing device of the patient (e.g., watch, phone, or other wearable devices) may be configured to confirm whether the patient is experiencing the acute health event, and in response control the output of the alert. The computing device may determine one or more physical states of the patient based on sensed data from one or more sensors, confirm that the patient is not experiencing the acute health event based on the determined one or more physical states, and output information based on the confirmation that the patient is not experiencing the acute health event. For instance, the computing device may output instructions to cease an alert (e.g., stop an alert that is ongoing), prevent an output of the alert (e.g., stop the alert from starting), or delay the output of the alert (e.g., wait until further confirmation or additional data can be gathered before starting the alert). In some examples, the computing device may deprioritize the alert (e.g., cease, prevent, or delay the alert), while allowing for another alert to output. For instance, the computing device may cease, prevent, or delay a higher-level alert (e.g., alert that contacts emergency medical services), and instead output a lower-level alert (e.g., alert that instructs the patient to schedule a doctor visit).

In this way, the example techniques improve the technology of detection and confirmation of the acute health event with techniques integrated in a practical application. For instance, the computing device may be configured to control the alert so as to prioritize alerts for confirmed cases of the acute health event, while deprioritizing (e.g., ceasing, preventing, or delaying) alerts for unconfirmed cases of the acute health event.

In one example, this disclosure describes a device of a patient includes an antenna configured to wirelessly receive communication from a medical device; and processing circuitry coupled to the antenna and configured to: determine that the received communication indicates that a patient is experiencing an acute health event; in response to the determination, determine one or more physical states of the patient based on sensed data from one or more sensors; confirm that the patient is not experiencing the acute health event based on the determined one or more physical states; and output information based on the confirmation that the patient is not experiencing the acute health event.

In another example, this disclosure describes a method of acute health event confirmation, the method includes receiving, with one or more devices of a patient, communication from a medical device; determining, with the one or more devices of the patient, that the received communication indicates that the patient is experiencing an acute health event; in response to the determination, determining, with the one or more devices of the patient, one or more physical states of the patient based on sensed data from one or more sensors; confirming, with the one or more devices of the patient, that the patient is not experiencing the acute health event based on the determined one or more physical states; and outputting, with the one or more devices, information based on the confirmation that the patient is not experiencing the acute health event.

In another example, this disclosure describes a computer-readable storage medium storing instructions thereon that when executed cause one or more processors to: determine that received communication from a medical device indicates that a patient is experiencing an acute health event; in response to the determination, determine one or more physical states of the patient based on sensed data from one or more sensors; confirm that the patient is not experiencing the acute health event based on the determined one or more physical states; and output information based on the confirmation that the patient is not experiencing the acute health event.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
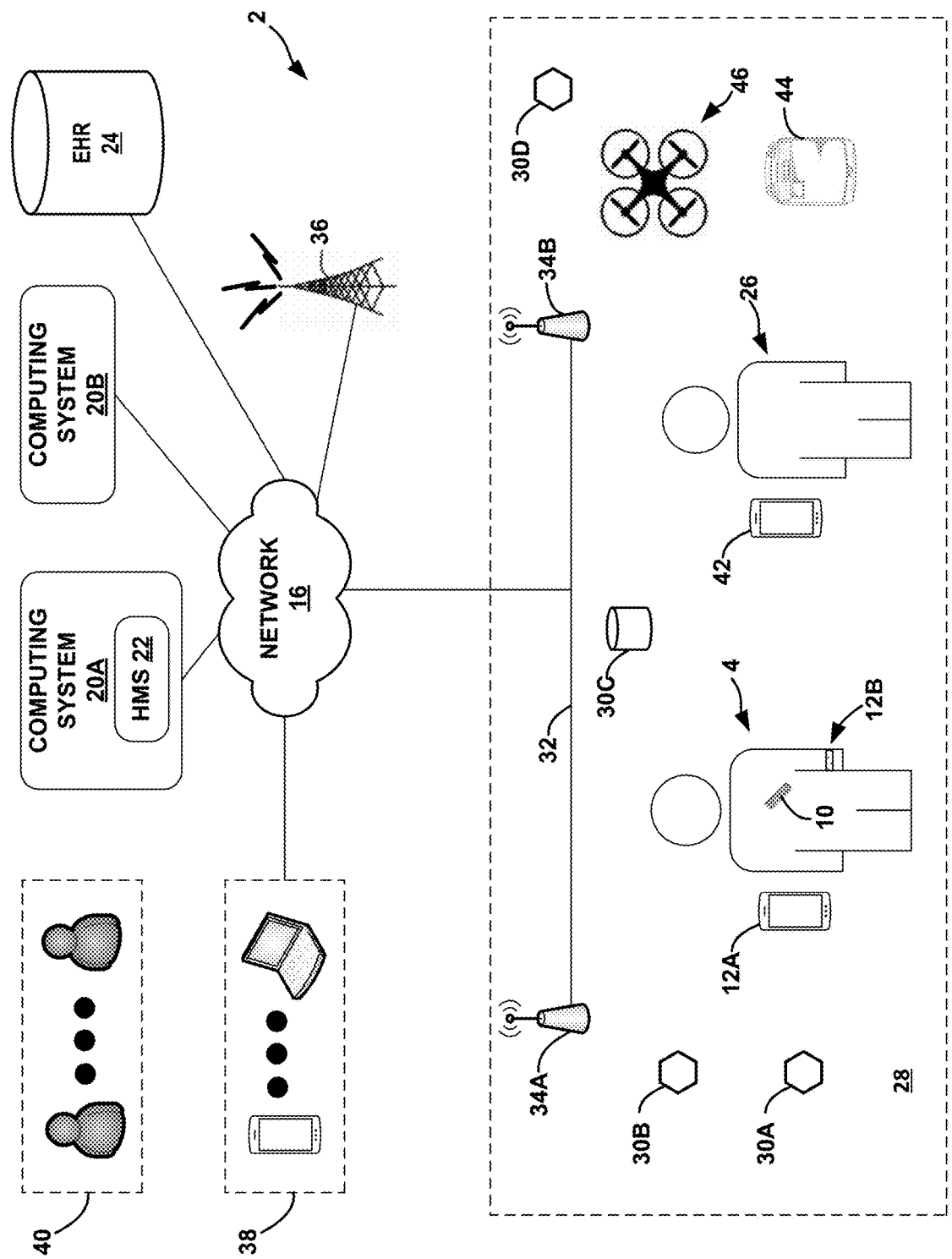
FIG. 1 is a block diagram illustrating an example system configured detect acute health events of a patient, and to respond to such detections, in accordance with one or more techniques of this disclosure.

A variety of types of implantable and medical devices detect arrhythmia episodes and other acute health events (e.g., sudden cardiac arrest (SCA)) based on sensed ECGs and, in some cases, other physiological signals. External devices that may be used to non-invasively sense and monitor ECGs and other physiological signals include wearable devices with electrodes configured to contact the skin of the patient, such as patches, watches, or necklaces. Such external devices may facilitate relatively longer-term monitoring of patient health during normal daily activities.

Implantable medical devices (IMDs) also sense and monitor ECGs and other physiological signals, and detect acute health events such as episodes of arrhythmia, cardiac arrest, myocardial infarction, stroke, and seizure. Example IMDs include pacemakers and implantable cardioverter-defibrillators, which may be coupled to intravascular or extravascular leads, as well as pacemakers with housings configured for implantation within the heart, which may be leadless. Some IMDs do not provide therapy, such as implantable patient monitors. One example of such an IMD is the Reveal LINQ II™ Insertable Cardiac Monitor (ICM), available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

As described in more detail, this disclosure describes example techniques of utilizing an external device (e.g., a computing device of a patient) to confirm whether the patient is experiencing an acute health event (e.g., SCA). By confirming whether the patient is experiencing the acute health event, the computing device of the patient may control an alert. In one or more examples, the computing device may determine one or more physical states of the patient to confirm whether the patient is experiencing the acute health event. Based on the confirmation, the computing device may cease, prevent, or delay the alert.

The physical states of the patient may include internal physical states and external physical states. Internal physical states refer to example physical states that cannot be determined simply by observing (e.g., looking at) the patient. For instance, an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern cannot be determined by looking at the patient. External physical states refer to example physical states that can be determined simply by observing (e.g., looking at) the patient. For instance, the posture of the patient, whether eye(s) are open, facial tone (e.g., whether there is facial droop due to stroke), skin (e.g., face) color, or whether the patient fell are examples of external physical states that can be determined simply by observing the patient.

It should be understood that although external physical states are described as states that can be determined by looking at someone and internal physical states are described as states that cannot be determined by looking at someone, the example techniques do not require an observer of the patient. Rather, the example techniques may utilize sensors (e.g., within the computing device or sensors that output to the computing device) that sense the external physical state of the patient and/or the internal physical state of the patient, and the computing device may utilize the sensed data from the one or more sensors to determine the one or more physical states.

In some techniques, the IMD may cause output of an alert in response to detection of the acute health event. Examples of the alert may be a call for emergency services (e.g., via the computing device), an audible or visual alert via the computing device, or other types of alerts. However, such alerts may be unnecessary or may be initially desired but later may not be needed. For example, the acute health event may mitigate itself so that emergency services are not needed. As another example, there may be a false identification of the acute health event.

In accordance with examples described in this disclosure, the computing device may confirm that the patient is not experiencing the acute health event (e.g., SCA) based on the determined one or more physical states, and output information based on the confirmation that the patient is not experiencing the acute health event. For example, the computing device may be configured to output instructions to cease an alert, prevent an output of the alert, or delay the output of the alert. As another example, the computing device may be configured to cause at least one of the medical device (e.g., IMD) or the computing device to output information to an emergency response system indicating that the patient is not experiencing SCA. For instance, if the alert already started, the computing device may output a follow up message to the emergency response system or to computing devices of bystanders indicating that emergency services are no longer needed.

FIG. 1 is a block diagram illustrating an example system 2 configured detect acute health events of a patient 4, and to respond to such detection, in accordance with one or more techniques of this disclosure. As used herein, the terms "detect," "detection," and the like may refer to detection of an acute health event presently (at the time the data is collected) being experienced by patient 4, as well as detection based on the data that the condition of patient 4 is such that they have a suprathreshold likelihood of experiencing the event within a particular timeframe, e.g., prediction of the acute health event. The example techniques may be used with one or more patient sensing devices, e.g., IMD 10, which may be in wireless communication with one or more patient computing devices, e.g., patient computing devices 12A and 12B (collectively, "patient computing devices 12"). Although not illustrated in FIG. 1, IMD 10 includes electrodes and other sensors to sense physiological signals of patient 4, and may collect and store sensed physiological data based on the signals and detect episodes based on the data.

IMD 10 may be implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. One example of IMD 10 is an insertable loop recorder (ILR). In some examples, IMD 10 takes the form of the LINQ II™ ICM. Although described primarily in the context of examples in which IMD 10 takes the form of an ICM, the techniques of this disclosure may be implemented in systems including any one or more implantable or external medical devices, including monitors, pacemakers, defibrillators, wearable external defibrillators, neurostimulators, or drug pumps. Furthermore, although described primarily in the context of examples including a single implanted patient sensing device, in some examples a system includes one or more patient sensing devices, which may be implanted within patient 4 or external to (e.g., worn by) patient 4.

Computing device(s) 12 may transmit data, including data retrieved from IMD 10, to computing system(s) 20 via network 16. The data may include sensed data, e.g., values of physiological parameters measured by IMD 10 and, in some cases one or more of computing devices 12, data regarding episodes of arrhythmia or other acute health events detected by IMD 10 and computing device(s) 12, and other physiological signals or data recorded by IMD 10 and/or computing device(s) 12. Values of physiological parameters measured by IMD 10 or one or more computing devices 12 are examples of values or data of one or more physical states of patient 4. As described in more detail below, there may be additional examples of physical states of patient 4, such as posture, whether eye(s) are open, facial tone (e.g., whether there is droop in facial tone), whether patient 4 fell, color of skin (e.g., face) of patient 4, whether patient 4 is able to provide coherent words, etc. Such examples of physical states may not necessarily be physiological parameters. That is, the one or more physical states of patient 4 include examples of physiological parameters and non-physiological parameters. Examples of physiological parameters may be considered as internal physical states, and some other physical states may be considered as external physical states.

As described above, internal physical states refer to example physical states that cannot be determined simply by observing (e.g., looking at) patient 4. Physiological parameters are examples of internal physical states because physiological parameters cannot be determined simply by observing patient 4. For instance, an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern cannot be determined by looking at patient 4. External physical states refer to example physical states that can be determined simply by observing (e.g., looking at) patient 4. For instance, the posture of patient 4, whether eye(s) are open (e.g., an eye opening), face color (e.g., skin color), facial tone of patient 4 (e.g., whether there is facial droop), asymmetrical face or body response of patient 4, whether patient 4 fell, whether patient 4 can speak coherently are examples of external physical states that can be determined simply by observing the patient.

Although external physical states are described as states that can be determined by observing someone without needing physiological parameters and internal physical states are described as states that cannot be determined by observing at someone and need physiological parameters, the example techniques do not require an observer of patient 4. Rather, the example techniques may utilize sensors (e.g., within one or more computing devices 12 or sensors that output to the computing devices 12 include IoT devices 30) that sense the external physical state of patient 4 and/or the internal physical state of patient 4, and one or more computing devices 12 may utilize the sensed data from the one or more sensors to determine the one or more physical states.

HMS 22 may also retrieve data regarding patient 4 from one or more sources of electronic health records (EHR) 24 via network. EHR 24 may include data regarding historical (e.g., baseline) physiological parameter values, previous health events and treatments, disease states, comorbidities, demographics, height, weight, and body mass index (BMI), as examples, of patients including patient 4. HMS 22 may use data from EHR 24 to configure algorithms implemented by IMD 10 and/or computing devices 12 to detect acute health events for patient 4. In some examples, HMS 22 provides data from EHR 24 to computing device(s) 12 and/or IMD 10 for storage therein and use as part of their algorithms for detecting acute health events.

Network 16 may include one or more computing devices, such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 16 may include one or more networks administered by service providers, and may thus form part of a large-scale public network infrastructure, e.g., the Internet. Network 16 may provide computing devices and systems, such as those illustrated in FIG. 1, access to the Internet, and may provide a communication framework that allows the computing devices and systems to communicate with one another. In some examples, network 16 may include a private network that provides a communication framework that allows the computing devices and systems illustrated in FIG. 1 to communicate with each other, but isolates some of the data flows from devices external to the private network for security purposes. In some examples, the communications between the computing devices and systems illustrated in FIG. 1 are encrypted.

As will be described herein, IMD 10 may be configured to detect acute health events of patient 4 based on data sensed by IMD 10 and, in some cases, other data, such as data sensed by computing devices 12A and/or 12B, and data from EHR 24. In response to detection of an acute health event, IMD 10 may wirelessly transmit a message to one or both of computing devices 12A and 12B. The message may indicate that IMD 10 detected an acute health event of the patient. The message may indicate a time that IMD 10 detected the acute health event. The message may include physiological data collected by IMD 10, e.g., data which lead to detection of the acute health event, data prior to detection of the acute health event, and/or real-time or more recent data collected after detection of the acute health event. The physiological data may include values of one or more physiological parameters and/or digitized physiological signals. Examples of acute health events are a cardiac arrest, a ventricular fibrillation, a ventricular tachycardia, myocardial infarction, a pause in heart rhythm (asystole), or Pulseless Electrical Activity (PEA), acute respiratory distress syndrome (ARDS), a stroke, a seizure, or a fall.

In response to the message from IMD 10, computing device(s) 12 may output an alarm that may be visual and/or audible, and configured to immediately attract the attention of patient 4 or any person in environment 28 with patient 4, e.g., a bystander 26. Environment 28 may be a home, office, or place of business, or public venue, as examples. Computing device(s) 12 may also transmit a message to HMS 22 via network 16. The message may include the data received from IMD 10 and, in some cases, additional data collected by computing device(s) 12 or other devices in response to the detection of the acute health event by IMD 10. For example, the message may include a location of patient 4 determined by computing device(s) 12.

Other devices in the environment 28 of patient 4 may also be configured to output alarms or take other actions to attract the attention of patient 4 and, possibly, a bystander 26, or to otherwise facilitate the delivery of care to patient 4. For example, environment 28 may include one or more Internet of Things (IoT) devices, such as IoT devices 30A-30D (collectively "IoT devices 30") illustrated in the example of FIG. 1. IoT devices 30 may include, as examples, so called "smart" speakers, cameras, lights, locks, thermostats, appliances, actuators, controllers, or any other smart home (or building) devices. In the example of FIG. 1, IoT device 30C is a smart speaker and/or controller, which may include a display. IoT devices 30 may provide audible and/or visual alarms when configured with output devices to do so. As other examples, IoT devices 30 may cause smart lights throughout environment 28 to flash or blink and unlock doors. In some examples, IoT devices 30 that include cameras or other sensors may activate those sensors to collect data regarding patient 4, e.g., for evaluation of the condition of patient 4.

Computing device(s) 12 may be configured to wirelessly communicate with IoT devices 30 to cause IoT devices 30 to take the actions described herein. In some examples, HMS 22 communicates with IoT devices 30 via network 16 to cause IoT devices 30 to take the actions described herein, e.g., in response to receiving the alert message from computing device(s) 12 as described above. In some examples, IMD 10 is configured to communicate wirelessly with one or more of IoT devices 30, e.g., in response to detection of an acute health event when communication with computing devices 12 is unavailable. In such examples, IoT device(s) 30 may be configured to provide some or all of the functionality ascribed to computing devices 12 herein.

Environment 28 includes computing facilities, e.g., a local network 32, by which computing devices 12, IoT devices 30, and other devices within environment 28 may communicate via network 16, e.g., with HMS 22. For example, environment 28 may be configured with wireless technology, such as IEEE 802.11 wireless networks, IEEE 802.15 ZigBee networks, an ultra-wideband protocol, near-field communication, or the like. Environment 28 may include one or more wireless access points, e.g., wireless access points 34A and 34B (collectively, "wireless access points 34") that provide support for wireless communications throughout environment 28. Additionally or alternatively, e.g., when local network is unavailable, computing devices 12, IoT devices 30, and other devices within environment 28 may be configured to communicate with network 16, e.g., with HMS 22, via a cellular base station 36 and a cellular network.

In one or more examples described in this disclosure, there may be instances where there is benefit in ceasing the alarm (e.g., stopping or overriding the alarm), preventing the alarm from occurring, and/or delaying the alarm from occurring. Some example techniques utilize feedback from patient 4 to confirm that the alarm can be ceased, prevented, or delayed. In one or more examples described in this disclosure, computing device(s) 12 may be configured to confirm whether the patient is experiencing or not experiencing the acute health event based on one or more physical states.

As described above, IMD 10 may be configured to detect a possible acute health event, such as SCA, and may cause output of the alert. However, in some examples, output of the alert may be unnecessary. For instance, it may be possible for the acute health event to end or resolve to a less concerning issue. It may be possible that the detection of the acute health event is incorrect. Accordingly, there may be benefit in ceasing, preventing, or delaying the alert if the acute health event is resolved without emergency assistance or if the acute health event is not confirmed.

As an example, if the alert is already sent out, there may be a benefit in ceasing the alert, and sending a following message that the acute health event is resolved and medical services are no longer needed. For instance, there may be an update message to bystanders and 911 operator with new messages that medical services are not needed. As another example, if the acute health event cannot be confirmed, then there may be benefit in preventing the alert from being output. As another example, if the acute health event cannot be confirmed but there is still a possibility that patient 4 may be experiencing an acute health event, then there may be benefit in delaying the alert until there is additional data to confirm the acute health event.

In some examples, there may be multiple alerts of different priorities. For instance, a higher-level alerts (i.e., higher-priority alerts) may be for when there is confirmation that patient 4 is experiencing the acute health event to ensure timely medical services. However, there may also be lower-level alerts (i.e., lower-priority alerts) that request patient 4 to follow up with a physician if the acute health event cannot be confirmed. In some examples, there may be benefit in ceasing, preventing, or delaying the higher-level alerts while allowing lower-level indications to pass through. In some examples, a higher-level alert may have been output. However, if there is confirmation that patient 4 is not experiencing an acute health event that requires the higher-level alert, it may be possible to reclassify the risk to patient 4 as lower risk, and allowing for a lower-level alert to be outputted.

For instance, if patient 4 has a sudden cardiac arrest that is confirmed (e.g., by computing device(s) 12 and/or IoT devices 30), but later it is determined (e.g., by IMD 10, computing device(s) 12, and/or IoT devices 30) that the sudden cardiac arrest has spontaneously ended, an intermediate state may result. In this intermediate state, patient 4 may still need medical attention, but no longer in an emergency state. Patient 4 may need a work-up, trauma recovery from a fall, stabilization, etc., but no longer needs emergency life support. In this example, a lower-level alert requesting help from a fall, or a message to patient 4 to visit a physician may be output.

As described above, there may be benefits in confirming the acute health event, and controlling alerts, such as by deprioritizing alerts (e.g., ceasing, preventing, or delaying alerts). In some examples, it may be possible for IMD 10 to deprioritize the alerts. For instance, IMD 10 may detect a return to a slower, consistent rhythm with normal QRS morphology (i.e., the heart of patient 4 returned to beating normally). For instance, after a few heart beats, it may be possible that the QRS morphology is normal. In such cases, it may be possible for IMD 10 to deprioritize the alerts. However, in one or more examples, the processing circuitry (e.g., of computing devices 12A, 12B) may be configured to confirm whether the acute health event (e.g., SCA) is actually occurring to control an alert.

For example, computing device 12A and/or 12B include an antenna configured to wirelessly receive communication from a medical device (e.g., IMD 10). The processing circuitry (e.g., of computing device 12A and/or 12B) may determine that the received communication indicates that patient 4 is experiencing the acute health event (e.g., SCA). In response to the determination that the received communication indicates that patient 4 is experiencing the acute health event, the processing circuitry may determine one or more physical states of the patient based on sensed data from one or more sensors (e.g., part of computing devices 12A or 12B or other components), and confirm whether patient 4 is experiencing the acute health event.

In some examples, the processing circuitry may confirm whether patient 4 is experiencing the acute health event based on confidence by IMD 10 that patient 4 actually experienced the acute health event. As one example, if IMD 10 further outputs communication indicating high confidence that patient 4 is experiencing the acute health event, then the processing circuitry may bypass confirmation of whether patient 4 is experiencing the acute health event and cause an alert to be output. However, if IMD 10 further outputs communication indicating low confidence that patient 4 is experiencing the acute health event, then the processing circuitry may perform the example techniques to confirm whether patient 4 is experiencing the acute health event.

Based on the confirmation that patient 4 is experiencing the acute health event or confirmation that patient 4 is not experiencing the acute health event, the processing circuitry may output information. As one example, the processing circuitry may be configured to output instructions to cease an output of an alert, prevent the output of the alert, or delay the output of the alert. As one example, the processing circuitry may be configured to cause at least one of the medical device or computing device 12A and/or 12B to output information to an emergency response system (e.g., EMS) indicating that patient 4 is not experiencing the acute health event.

When patient 4 is experiencing the acute health event, there may be other indicators that can be used to confirm the occurrence of the acute health event. As an example, if patient 4 is experiencing SCA, the posture of patient 4 is likely to not be vertical, and patient 4 is likely to have his or her eyes closed. Patient 4 would have likely fallen down as well. The posture of patient 4, whether eyes of patient 4 are open or closed, the color of the face of patient 4, and whether patient 4 fell are all examples of external physical state of patient 4 (e.g., physical state of patient 4 that can be observed externally). In some cases, the face color (e.g., skin color) of patient 4 may also be paler than normal. As described below, changes in color (e.g., fluctuations) may also be analyzed using signal processing or machine learning techniques to estimate whether patient 4 is experiencing the acute health event.

In some examples, computing devices 12A or 12B may include one or more sensors such as accelerometers and/or inertial measurement units (IMUs). The sensed data from the accelerometers and/or IMUs may include posture data. To determine one or more physical states of patient 4 based on sensed data from one or more sensors, the processing circuitry may determine whether patient 4 is in a vertical posture based on the information indicative of the posture of patient 4. If patient 4 is in the vertical posture, then the processing circuitry may determine that it is unlikely that patient 4 is experiencing the acute health event. If patient 4 is not in the vertical posture, then the processing circuitry may determine that it is likely that patient 4 is experiencing the acute health event, such as when IMD 10 also determined that patient 4 is experiencing the acute health event.

As another example, the sensed data may be information indicative of a time-series of positioning of the patient. For example, the accelerometers and/or IMUs may be configured to generate a time-series of positioning of patient 4 (e.g., information that indicates the position of patient 4 over time). To determine the one or more physical states of the patient based on sensed data from one or more sensors, the processing circuitry may be configured to determine whether patient 4 fell based on the information indicative of the time-series of the positioning of patient 4.

For instance, if the time-series of positioning of patient 4 indicates that patient 4 fell down (e.g., was in vertical positioning and then very quickly on a position on the ground), the processing circuitry may determine that it is likely that patient 4 is experiencing the acute health event, such as when IMD 10 also determined that patient 4 is experiencing the acute health event. If the time-series of positioning of patient 4 indicates that patient 4 did not fall down (e.g., the positioning of patient 4 did not change over time or changed slowly over time), then the processing circuitry may determine that it is unlikely that patient 4 is experiencing the acute health event.

As another example, the one or more sensors may be a camera of computing device 12A or 12B or from IoT devices 30. The sensed data may be an image of a face of patient 4 captured with the camera. For instance, if the processing circuitry determines that the received communication from IMD 10 indicates that patient 4 is experiencing the acute health event, the processing circuitry may cause the camera to immediately capture images. As another example, IoT devices 30 may receive the communication form IMD 10 that indicates that patient 4 is experiencing the acute health event, a camera of one or more IoT devices 30 and may begin to capture images and transmit the images to one or more computing devices 12 or IoT devices 30 may process the captured imaged. There may be possibility that in the images that the camera captures that one of the images includes an image of the face of patient 4.

In such examples, to determine the one or more physical states of patient 4 based on sensed data from one or more sensors, the processing circuitry (e.g., of one or more computing devices 12 and/or IoT devices 30) may be configured to, at least one of, determine whether one or both eyes of patient 4 are open based on the image of the face, or determine a color of the face of patient 4. In such examples, the sensor may be the camera and the sensed data may be the images.

For example, the processing circuitry (e.g., of one or more computing devices 12 and/or IoT devices 30) may be configured to implement a face detection algorithm to detect the face and eyes from the images. The processing circuitry may compare the detected face to a pre-stored image of the face of patient 4 to confirm that the image is of patient 4. The processing circuitry may then evaluate a number or percentage of white pixels in the area of the image where the eyes of patient 4 should be. If the processing circuitry determines that number or percentage of white pixels in the area is greater than a threshold, then the eye(s) of patient 4 are open. If the processing circuitry determines that number or percentage of white pixels in the area is less than the threshold, then the eye(s) of patient 4 are closed.

If the eyes of patient 4 are open, then the processing circuitry may determine that it is unlikely that patient 4 is experiencing the acute health event. If the eyes of patient 4 are closed, then the processing circuitry may determine that it is likely that patient 4 is experiencing the acute health event, such as when IMD 10 also determined that patient 4 is experiencing the acute health event.

Similarly, the processing circuitry may determine a tint of the color of the face of patient 4 from the captured images. The processing circuitry may compare the color of the face of patient 4 to a pre-stored image of the face of patient 4. If there is no change in the tint of color of face of patient 4 or the amount of change is less than a threshold, the processing circuitry may determine that it is unlikely that patient 4 is experiencing the acute health event. If the amount of change in the tint of color of face of patient 4 is greater than the threshold, the processing circuitry may determine that is likely that patient 4 is experiencing the acute health event.

The skin color (e.g., face color) may vary based on blood flow, and other physiological parameters. If patient 4 is experiencing the acute health event there may be change in the physiological parameters, that may manifest as change in skin color. For example, the processing circuitry may determine changes in color (e.g., fluctuations), and estimate a pulse rate (e.g., via signal processing or machine learning techniques). Based on the estimated pulse rate, the processing circuitry may confirm whether patient 4 is experiencing or not experiencing the acute health event.

For instance, the processing circuitry may determine a change in skin color, such as face color, to determine whether there is a change in physiological parameters. Based on a determination that there is a change in physiological parameters, the processing circuitry may determine whether the change is sufficient to indicate that patient 4 is experiencing the acute health event or the change is caused by patient 4 experiencing the acute health event.

As one example, the one or more sensors may be a microphone of computing device 12A and/or 12B or a microphone of one or more IoT devices 30. The sensed data may be information indicative of sound captured with the microphone. To determine the one or more physical states of patient 4 based on sensed data from one or more sensors, the processing circuitry (e.g., of one or more computing devices 12 and/or IoT devices 30) may be configured to determine whether patient 4 is in a physical state for providing sound based on the sound captured with the microphone.

For instance, in response to determining that a received communication indicates that patient 4 is experiencing the acute health event, the processing circuitry may turn on the microphone of computing device 12A and/or 12B and/or one or more of IoT devices 30, and may start recording sound. The processing circuitry may analyze the sound to determine if the sound include coherent words from patient 4 (e.g., "I'm okay," or words one would have in a normal conversation). If the sound includes coherent words from patient 4, then it is less likely that patient 4 is not experiencing the acute health event. If the sound does not include coherent words from patient 4, then it is likely that patient 4 is experiencing the acute health event.

A microphone may be utilized in various ways to confirm whether patient 4 is experiencing the acute health event. As one example, the processing circuitry may utilize the sound captured by the microphone to identify agonal breathing. Agonal breathing is a labored breathing and may be associated with an acute health event, like SCA. In one or more examples, if the processing circuitry determines that the captured sound does not include agonal breathing sounds, the processing circuitry may determine that is less likely that patient 4 is experiencing the acute health event. However, if the captured sound includes agonal breathing sounds, the processing circuitry may determine that it is more likely that patient 4 is experiencing the acute health event.

The above describe some example ways in which the processing circuitry may confirm the acute health event based on one or more physical states (e.g., external physical states) of patient 4. The above example techniques may be used separately or combined together in various ways (e.g., the processing circuitry may evaluate the posture, whether patient 4 fell down, and sounds captured by the microphone to confirm the acute health event). Also, the above examples of the physical state of patient 4 were for external physical states (e.g., posture of patient 4, facial tone of patient 4, asymmetrical face or body response of patient 4, whether patient 4 fell, whether eyes of patient 4 are open or closed, the color of the face of patient 4, whether sound from patient 4 is coherent).

In some examples, rather than or in addition to utilizing the external physical state of patient 4, the processing circuitry may utilize the internal physical state of patient 4 to confirm the acute health event. Examples of the internal physical state of patient 4 include physiological parameters such as an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern. For instance, one or more computing devices 12 may include sensors for sensing an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern. Based on the sensed data from such sensors, the processing circuitry may confirm whether patient 4 is experiencing the acute health event.

The processing circuitry may also provide secondary processing to check whether IMD 10 is operating correctly. As one example, the one or more sensors may be one or more sensors of the medical device (e.g., IMD 10) for sensing at least one of a cardiac signal, neurological signal, and respiratory signal. The processing circuitry may be configured to receive a second instance of the communication from the medical device that includes information indicative of at least one of the cardiac signal, neurological signal, and respiratory signal. To determine one or more physical states of patient 4 based on sensed data from one or more sensors, the processing circuitry may be configured to determine a cardiac condition of patient 4 based on the information indicative of at least one of the cardiac signal, neurological signal, and respiratory signal.

For instance, IMD 10 may have determined that patient 4 is experiencing the acute health event based on at least one of a sensed cardiac signal, neurological signal, and respiratory signal. However, it may be possible that IMD 10 incorrectly determined that patient 4 is experiencing the acute health event. Accordingly, IMD 10 may output at least one of the cardiac signal, neurological signal, and respiratory signal to the processing circuitry (e.g., of computing device 12A, 12B, 18, or some other computing device or system) to recheck and confirm the acute health event. If the processing circuitry determines that patient 4 is not experiencing the acute health event based on the sensed data, it may be possible that IMD 10 provided a false positive of the acute health event.

In some examples, IMD 10 may output a subsequent cardiac signal, neurological signal, and/or respiratory signal to the processing circuitry. The processing circuitry may determine if the acute health event is no longer occurring. For example, the processing circuitry receives new ECG waveforms (e.g., which are examples of a cardiac signal) from IMD 10 and determines through post-processing that the acute health event (e.g., SCA) is no longer happening. For instance, ventricular tachycardias may "break" on their own after a few seconds. Processing circuitry receiving the new ECG waveforms to confirm that the acute health event (e.g., ventricular tachycardias) are not longer occurring may be beneficial to cease, prevent, or delay an alert.

Accordingly, in some examples, the received communication that indicates that patient 4 is experiencing the acute health event may be a first instance of the communication. The processing circuitry may be configured to receive a second instance of the communication that includes information indicative of the cardiac signal. This second instance of the communication may be the cardiac waveform that IMD 10 used to determine that patient 4 is experiencing an acute health event so that the processing circuitry can confirm the acute health event. As another example, the second instance of communication may be the new cardiac waveform (e.g., new ECG) that the processing circuitry uses to determine if the acute health event is no longer happening. The second instance of communication or there may be multiple instances of communication to provide both cardiac waveform that IMD 10 used to determine that patient 4 is experiencing an acute health event and the new cardiac waveform. To determine one or more physical states of the patient based on sensed data from one or more sensors, the processing circuitry may be configured to determine a cardiac condition of the patient based on the information indicative of the cardiac signal (e.g., new cardiac signal or cardiac signal used by IMD 10 to determine that patient 4 is experiencing the acute health event).

There may be other ways in which to confirm that patient 4 is not experiencing the acute health event. As one example, the processing circuitry may be configured to output a request for patient feedback, and to confirm that patient 4 is not experiencing the acute health event, the processing circuitry may be configured to confirm that patient 4 is not experiencing the acute health event based on the determination of the one or more physical states and based on reception of the patient feedback responsive to the request for patient feedback. For instance, the processing circuitry may request patient 4 to say aloud sentences like "I am okay," and the processing circuitry may utilize the additional feedback to fully confirm that patient 4 is not experiencing the acute health event. As additional examples of feedback, patient 4 may tap over his or her body proximate to where IMD 10 is located a series of special taps to indicate that patient 4 is not experiencing the acute health event, patient 4 may wave his or her arm or body to indicate that patient 4 is not experiencing the acute health event, or other ways in which the processing circuitry receives input from patient 4 that patient 4 is conscious and asymptomatic.

In addition to or instead of the examples provided above, there may be other situations where the alert should be deprioritized. For instance, if the processing circuitry determines that patient 4 is already receiving medical services, then the processing circuitry may cease, prevent, or delay output of an alert. As one example, the processing circuitry may determine a geofence around patient 4. If the processing circuitry determines that medical service professionals are within the geofence (e.g., based on communication from devices with environment 28 or HMS 22 to the processing circuitry), then the processing circuitry may determine that medical services are being provided to patient 4. For instance, once EMS is on the site, retriggering of alerts or dialing an emergency system (e.g., dialing 911 in North America) should be avoided. By determining that medical services are being provided, the processing circuitry may deprioritize the alerts.

Computing device(s) 12, and in some examples IoT devices 30, may include input devices and interfaces to allow a user to override the alarm in the event the detection of the acute health event by IMD 10 was false. For instance, in addition to processing circuitry of computing device(s) 12 and/or IoT devices 30 confirming whether patient 4 is experiencing the acute health event, patient 4 may be able to provide feedback indicating whether patient 4 is experiencing the acute health condition. In some examples, one or more of computing device(s) 12 and IoT device(s) 30 may implement an event assistant. The event assistant may provide a conversational interface for patient 4 and/or bystander 26 to exchange information with the computing device or IoT device. The event assistant may query the user regarding the condition of patient 4 in response to receiving the alert message from IMD 10. Responses from the user may be used to confirm or override detection of the acute health event by IMD 10, or to provide additional information about the acute health event or the condition of patient 4 more generally that may improve the efficacy of the treatment of patient 4. For example, information received by the event assistant may be used to provide an indication of severity or type (differential diagnosis) for the acute health event. The event assistant may use natural language processing and context data to interpret utterances by the user. In some examples, in addition to receiving responses to queries posed by the assistant, the event assistant may be configured to respond to queries posed by the user. For example, patient 4 may indicate that they feel dizzy and ask the event assistant, "how am I doing?".

In some examples, computing device(s) 12 and/or HMS 22 may implement one or more algorithms to evaluate the sensed physiological data received from IMD 10, and in some cases additional physiological or other data sensed or otherwise collected by the computing device(s) or IoT devices 30, to confirm or override the detection of the acute health event by IMD 10. Examples of the sensed data includes data of the external physical state of patient 4, and data of the internal physical state of patient 4, as described above. In some examples, computing device(s) 12 and/or computing system(s) 20 may have greater processing capacity than IMD 10, enabling more complex analysis of the data. In some examples, the computing device(s) 12 and/or HMS 22 may apply the data to a machine learning model or other artificial intelligence developed algorithm, e.g., to determine whether the data is sufficiently indicative of the acute health event.

In examples in which computing device(s) 12 are configured perform an acute health event confirmation analysis, computing device(s) 12 may transmit alert messages to HMS 22 and/or IoT devices 30 in response to confirming the acute health event. In some examples, computing device(s) 12 may be configured to transmit the alert messages prior to completing the confirmation analysis, and transmit cancellation messages (e.g., to cease, prevent, or delay alerts) in response to the analysis overriding the detection of the acute health event by IMD 10. HMS 22 may be configured to perform a number of operations in response to receiving an alert message from computing device(s) 12 and/or IoT device(s) 30. HMS 22 may be configured to cancel such operations in response to receiving a cancellation message from computing device(s) 12 and/or IoT device(s) 30.

For example, HMS 22 may be configured to transmit alert messages to one or computing devices 38 associated with one or more care providers 40 via network 16. Care providers may include emergency medical systems (EMS) and hospitals, and may include particular departments within a hospital, such as an emergency department, catheterization lab, or a stroke response department. Computing devices 38 may include smartphones, desktop, laptop, or tablet computers, or workstations associated with such systems or entities, or employees of such systems or entities. The alert messages may include any of the data collected by IMD 10, computing device(s) 12, and IoT device(s) 30, including sensed physiological data, time of the acute health event, location of patient 4, and results of the analysis by IMD 10, computing device(s) 12, IoT device(s) 30, and/or HMS 22. The information transmitted from HMS 22 to care providers 40 may improve the timeliness and effectiveness of treatment of the acute health event of patient 4 by care providers 40. In some examples, instead of or in addition to HMS 22 providing an alert message to one or more computing devices 38 associated with an EMS care provider 40, computing device(s) 12 and/or IoT devices 30 may be configured to automatically contact EMS (e.g., autodial in North America, using a telephone system to contact 911 call center), in response to receiving an alert message from IMD 10. Again, such operations may be cancelled by patient 4, bystander 26, or another user via a user interface of computing device(s) 12 or IoT device(s) 30, or automatically cancelled by computing device(s) 12 based on a confirmatory analysis performed by the computing device(s) overriding the detection of the acute health event by IMD 10.

Similarly, HMS 22 may be configured to transmit an alert message to computing device 42 of bystander 26, which may improve the timeliness and effectiveness of treatment of the acute health event of patient 4 by bystander 26. Computing device 42 may be similar to computing devices 12 and computing devices 38, e.g., a smartphone. In some examples, HMS 22 may determine that bystander 26 is proximate to patient 4 based on a location of patient 4, e.g., received from computing device(s) 12, and a location of computing device 42, e.g., reported to HMS 22 by an application implemented on computing device 42. In some examples, HMS 22 may transmit the alert message to any computing devices 42 in an alert area determined based on the location of patient 4, e.g., by transmitting the alert message to all computing devices in communication with base station 36.

Computing device 42 may be another example of a device configured to perform the example techniques described in this disclosure. As one example, computing device 42 may be configured to output information based on the confirmation that patient 4 is or is not experiencing the acute health event. For instance, computing device 42 of bystander 26 (e.g., caregiver device) may allow an alert to cease, prevent, or delay. As one example, if 911 has been dialed (e.g., emergency services have been requested), computing device 42 may be configured to output information that patient 4 is not experiencing the acute health event (e.g., disable the alert or notify that emergency services are not needed).

For instance, one or more of computing device(s) 12 and/or IoT devices 30 may output information indicative of the physical states of patient 4 based on the sensed data from one or more sensors to computing device 42. Computing device 42 may determine one or more physical states of patient 4 based on sensed data and confirm that patient 4 is not experiencing the acute health event based on the determined one or more physical states. In some examples, rather than both determining physical state and confirming that patient 4 is or is not experiencing the acute health event, computing device 42 may perform at least one of determining physical state or confirming that patient 4 is not experiencing the acute health event.

In some examples, computing device 42 may output information based on the confirmation that patient 4 is not experiencing the acute health event. It may also be possible that one or more of computing devices 12 and/or IoT devices 30 confirm that patient 4 is not experiencing the acute health event and output information of the confirmation to computing device 42. Computing device 42 may then output further information (e.g., output instructions to cease an output of an alert, prevent the output of the alert, or delay the output of the alert or output information to an emergency response system indicating that the patient is not experiencing the acute health event).

In some examples, the alert message to bystander 26 may be configured to assist a layperson in treating patient. For example, the alert message to bystander 26 may include a location (and in some cases a description) of patient 4, the general nature of the acute health event, directions for providing care to patient 4, such as directions for providing cardio-pulmonary resuscitation (CPR), a location of nearby medical equipment for treatment of patient 4, such as an automated external defibrillator (AED) 44, and instructions for use of the equipment. AED 44 may be a life vest with electrodes to provides the defibrillation. In some examples, computing device(s) 12, IoT device(s) 30, and/or computing device 42 may implement an event assistant configured to use natural language processing and context data to provide a conversational interface for bystander 26. The assistant may provide bystander 26 with directions for providing care to patient 4, and respond to queries from bystander 26 about how to provide care to patient 4.

In some examples, HMS 22 may mediate bi-directional audio (and in some cases video) communication between care providers 40 and patient 4 or bystander 26. Such communication may allow care providers 40 to evaluate the condition of patient 4, e.g., through communication with patient 4 or bystander 26, or through use of a camera or other sensors of the computing device or IoT device, in advance of the time they will begin caring for the patient, which may improve the efficacy of care delivered to the patient. Such communication may also allow the care providers to instruct bystander 26 regarding first responder treatment of patient 4.

In some examples, HMS 22 may control dispatch of a drone 46 to environment 28, or a location near environment 28 or patient 4. Drone 46 may be a robot and/or unmanned aerial vehicle (UAV). Drone 46 may be equipped with a number of sensors and/or actuators to perform a number of operations. For example, drone 46 may include a camera or other sensors to navigate to its intended location, identify patient 4 and, in some cases, bystander 26, and to evaluate a condition of patient. In some examples, drone 46 may include user interface devices to communicate with patient 4 and/or bystander 26. In some examples, drone 46 may provide directions to bystander 26, to the location of patient 4 and regarding how to provide first responder care, such as CPR, to patient 4. In some examples, drone 46 may carry medical equipment, e.g., AED 44, and/or medication to the location of patient 4.

HMS 22 may be configured to cease output of the alert, prevent the output of the alert, or delay the output of the alert. For instance, HMS 22 may receive confirmation that patient 4 is not experiencing the acute health event, and output information based on the confirmation that the patient is not experiencing the acute health event. For example, HMS 22 may output to computing devices 38 of care providers 40 that there is confirmation that patient 4 is not experiencing the acute health event. In response, computing devices 38, care providers 40, and/or HMS 22 may cease output of the alert, prevent the output of the alert, or delay the output of the alert. This way, care providers 40 know that there is no immediate emergency. For instance, HMS 22 may output information to an emergency response system (e.g., computing devices 38 of care providers 40) indicating that patient 4 is not experiencing the acute health event.

Although described herein in the context of example IMD 10, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, a neurostimulator, or a drug delivery device.

Figure 2:
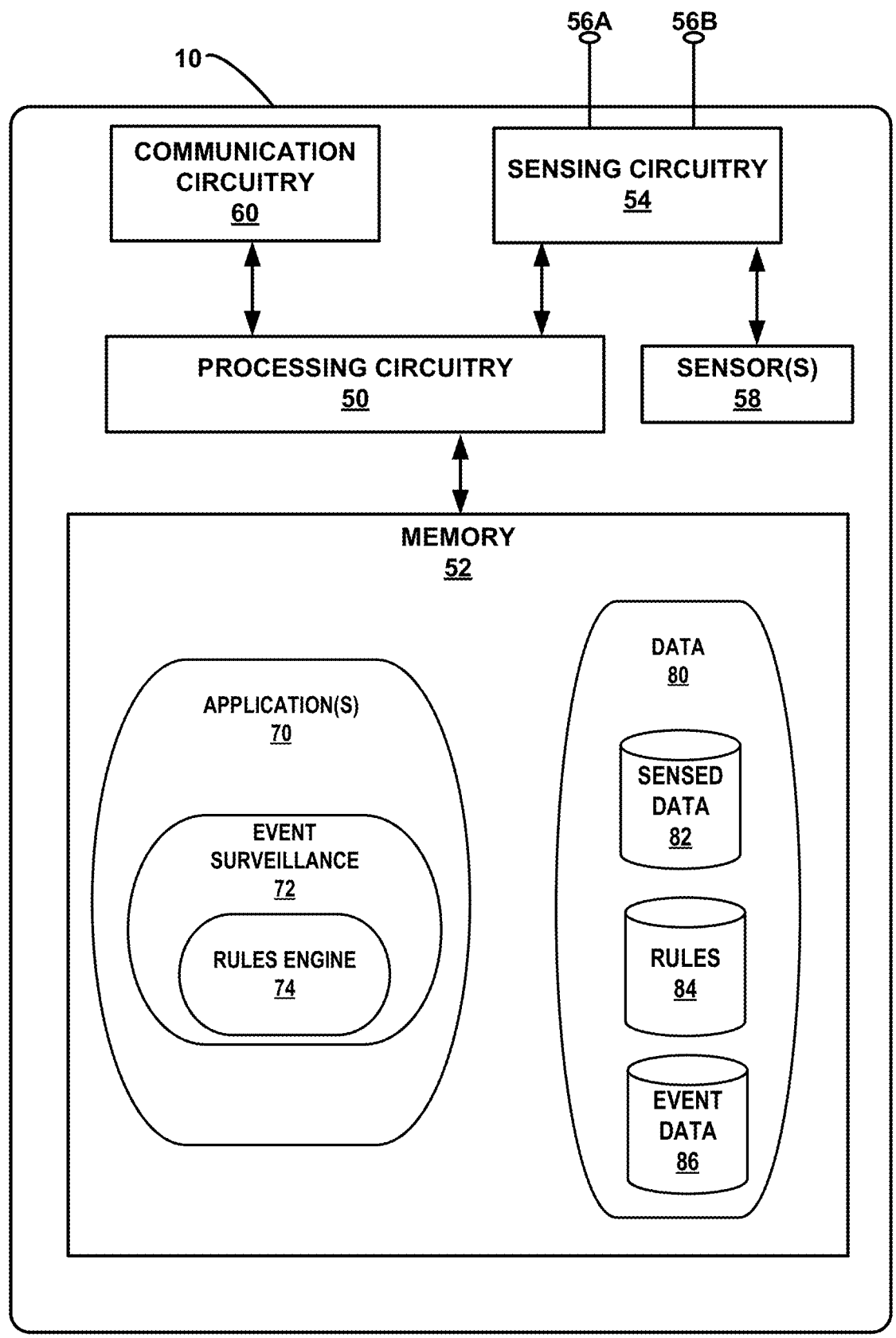
FIG. 2 is a block diagram illustrating an example configuration of a patient sensing device that operates in accordance with one or more techniques of the present disclosure.

FIG. 2 is a block diagram illustrating an example configuration of IMD 10 of FIG. 1. As shown in FIG. 2, IMD 10 includes processing circuitry 50, memory 52, sensing circuitry 54 coupled to electrodes 56A and 56B (hereinafter, "electrodes 56") and one or more sensor(s) 58, and communication circuitry 60.

Processing circuitry 50 may include fixed function circuitry and/or programmable processing circuitry. Processing circuitry 50 may include any one or more of a microprocessor, a controller, a graphics processing unit (GPU), a tensor processing unit (TPU), a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more GPUs, one or more TPUs, one or more DSPs, one or more ASICs, or one or more FPGAs, as well as other discrete or integrated logic circuitry. The functions attributed to processing circuitry 50 herein may be embodied as software, firmware, hardware, or any combination thereof. In some examples, memory 52 includes computer-readable instructions that, when executed by processing circuitry 50, cause IMD 10 and processing circuitry 50 to perform various functions attributed herein to IMD 10 and processing circuitry 50. Memory 52 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 54 may monitor signals from electrodes 56 in order to, for example, monitor electrical activity of a heart of patient 4 and produce ECG data for patient 4. In some examples, processing circuitry 50 may identify features of the sensed ECG, such as heart rate, heart rate variability, intra-beat intervals, and/or ECG morphologic features, to detect an episode of cardiac arrhythmia of patient 4. Processing circuitry 50 may store the digitized ECG and features of the ECG used to detect the arrhythmia episode in memory 52 as episode data for the detected arrhythmia episode.

In some examples, sensing circuitry 54 measures impedance, e.g., of tissue proximate to IMD 10, via electrodes 56. The measured impedance may vary based on respiration and a degree of perfusion or edema. Processing circuitry 50 may determine physiological data relating to respiration, perfusion, and/or edema based on the measured impedance. As one example, sensing circuitry 54 may sense impedance (e.g., subcutaneous or intra-cardiac) to sense a cardiac pulse. Impedance may also be indicative the presence or absence of breathing or gasping.

In some examples, IMD 10 includes one or more sensors 58, such as one or more accelerometers, microphones, optical sensors, temperature sensors, and/or pressure sensors. In some examples, sensing circuitry 54 may include one or more filters and amplifiers for filtering and amplifying signals received from one or more of electrodes 56 and/or sensors 58. In some examples, sensing circuitry 54 and/or processing circuitry 50 may include a rectifier, filter and/or amplifier, a sense amplifier, comparator, and/or analog-to-digital converter. Processing circuitry 50 may determine physiological data, e.g., values of physiological parameters of patient 4, based on signals from sensors 58, which may be stored in memory 52.

In some examples, processing circuitry 50 and/or processing circuitry of other devices (e.g., computing device(s) 12, one or more IoT devices 30) may utilize the output from one or more sensors 58 to confirm whether patient 4 is experiencing the acute health event. One or more sensors 58 may sense heart sounds. For example, one or more sensors 58 may include an accelerometer or a microphone used to pick up the heart sounds (e.g., the accelerometer may detect the movement of the heart, and the microphone may detect the sound the heart makes when beating). If there are no heart sounds, then processing circuitry 50 or other processing circuitry may confirm that patient 4 is having an acute health event. If there are heart sounds, then processing circuitry 50 or other processing circuitry may confirm that patient 4 is not having an acute health event.

Memory 52 may store applications 70 executable by processing circuitry 50, and data 80. Applications 70 may include an acute health event surveillance application 72. Processing circuitry 50 may execute event surveillance application 72 to detect an acute health event of patient 4 based on combination of one or more of the types of physiological data described herein, which may be stored as sensed data 82. In some examples, sensed data 82 may additionally include data sensed by other devices, e.g., computing device(s) 12, and received via communication circuitry 60. Event surveillance application 72 may be configured with a rules engine 74. Rules engine 74 may apply rules 84 to sensed data 82. Rules 84 may include one or more models, algorithms, decision trees, and/or thresholds. In some cases, rules 84 may be developed based on machine learning.

As examples, event surveillance application 72 may detect a cardiac arrest (e.g., sudden cardiac arrest (SCA)), a ventricular fibrillation, a ventricular tachycardia, or a myocardial infarction, a pause in heart rhythm (asystole) (e.g., a cardiac pause of asystole), or Pulseless Electrical Activity (PEA), acute respiratory distress syndrome (ARDS), based on an ECG and/or other physiological data indicating the electrical or mechanical activity of the heart of patient 4 (FIG. 1). In some examples, event surveillance application 72 may detect stroke based on such cardiac activity data. In some examples, sensing circuitry 54 may detect brain activity data, e.g., an electroencephalogram (EEG) via electrodes 56, and event surveillance application 72 may detect stroke or a seizure based on the brain activity alone, or in combination with cardiac activity data or other physiological data. In some examples, event surveillance application 72 detects whether the patient has fallen based on data from an accelerometer alone, or in combination with other physiological data. When event surveillance application 72 detects an acute health event, event surveillance application 72 may store the sensed data 82 that lead to the detection (and in some cases a window of data preceding and/or following the detection) as event data 86.

In some examples, in response to detection of an acute health event, processing circuitry 50 transmits, via communication circuitry 60, event data 86 for the event to computing device(s) 12 and/or IoT devices 30 (FIG. 1). This transmission may be included in a message indicating the acute health event, as described herein. Transmission of the message may occur on an ad hoc basis and as quickly as possible. Communication circuitry 60 may include any suitable hardware, firmware, software, or any combination thereof for wirelessly communicating with another device, such as computing devices 12 and/or IoT devices 30.

In one or more example techniques, communication circuitry 60 may output a communication to a computing device (e.g., computing device 12 or IoT device 30). In some examples, communication circuitry 60 may also include sensed data such as a cardiac signal, neurological signal, respiratory signal, and/or accelerometer data. The computing device (e.g., computing device 12 or IoT device 30) may be configured to determine one or more physical states of patient 4 based on the sensed data from the one or more sensors (e.g., cardiac signal, neurological signal, respiratory signal, or accelerometer data), and confirm whether patient 4 is experiencing the acute health event based on the determined one or more physical states.

Figure 3:
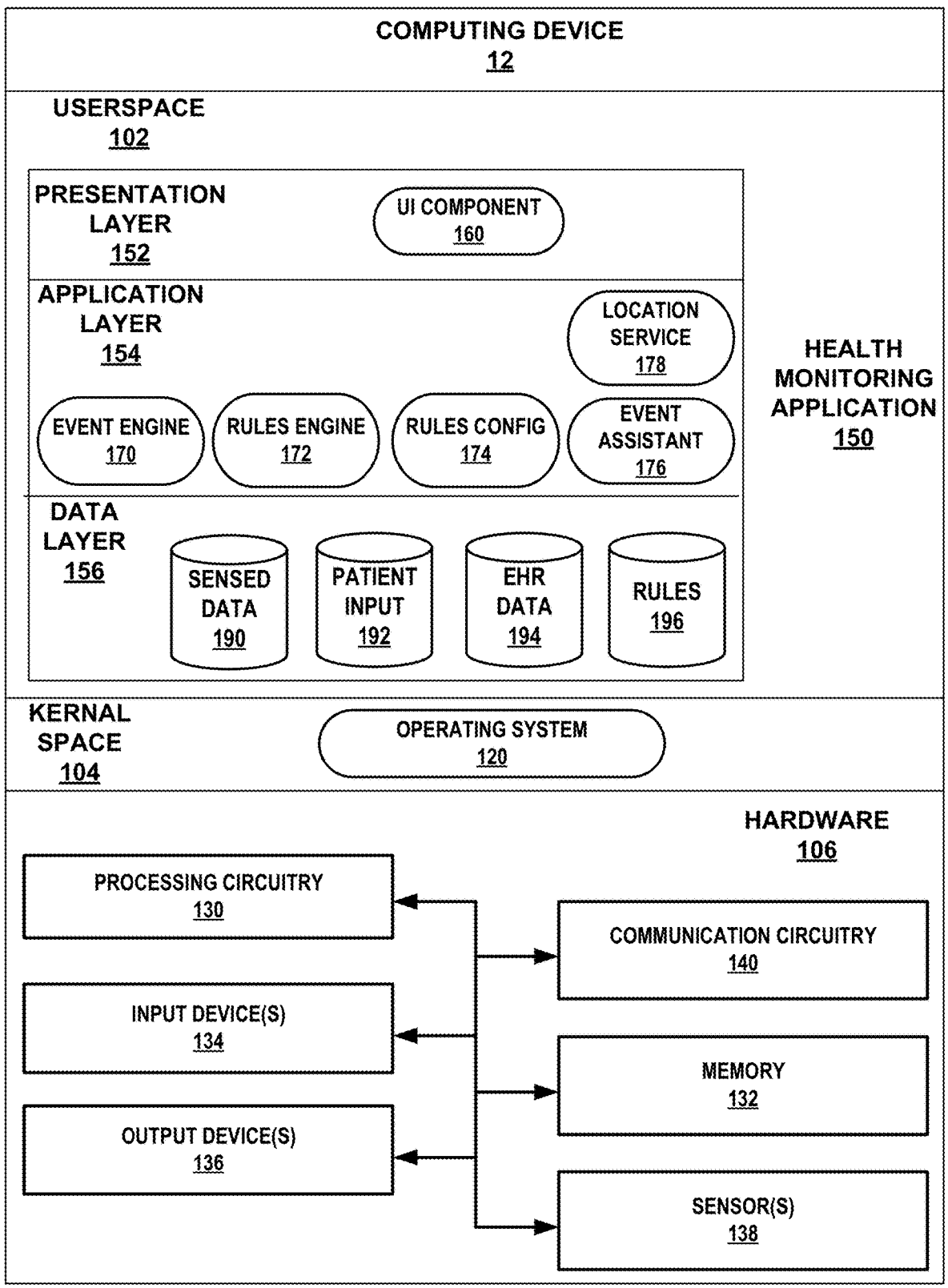
FIG. 3 is block diagram illustrating an example configuration of a computing device that operates in accordance with one or more techniques of the present disclosure.

FIG. 3 is a block diagram illustrating an example configuration of a computing device 12 of patient 4, which may correspond to either (or both operating in coordination) of computing devices 12A and 12B illustrated in FIG. 1. In some examples, computing device 12 takes the form of a smartphone, a laptop, a tablet computer, a personal digital assistant (PDA), a smartwatch or other wearable computing device (e.g., a wearable ring, wearable health sensor, or smart clothing). In some examples, IoT devices 30 may be configured similarly to the configuration of computing device 12 illustrated in FIG. 3.

As shown in the example of FIG. 3, computing device 12 may be logically divided into user space 102, kernel space 104, and hardware 106. Hardware 106 may include one or more hardware components that provide an operating environment for components executing in user space 102 and kernel space 104. User space 102 and kernel space 104 may represent different sections or segmentations of memory 132, where kernel space 104 provides higher privileges to processes and threads than user space 102. For instance, kernel space 104 may include operating system 120, which operates with higher privileges than components executing in user space 102.

As shown in FIG. 3, hardware 106 includes processing circuitry 130, memory 132, one or more input devices 134, one or more output devices 136, one or more sensors 138, and communication circuitry 140. Although shown in FIG. 3 as a stand-alone device for purposes of example, computing device 12 may be any component or system that includes processing circuitry or other suitable computing environment for executing software instructions and, for example, need not necessarily include one or more elements shown in FIG. 3.

Processing circuitry 130 is configured to implement functionality and/or process instructions for execution within computing device 12. For example, processing circuitry 130 may be configured to receive and process instructions stored in memory 132 that provide functionality of components included in kernel space 104 and user space 102 to perform one or more operations in accordance with techniques of this disclosure. Examples of processing circuitry 130 may include, any one or more microprocessors, controllers, GPUs, TPUs, DSPs, ASICs, FPGAs, or equivalent discrete or integrated logic circuitry.

Memory 132 may be configured to store information within computing device 12, for processing during operation of computing device 12. Memory 132, in some examples, is described as a computer-readable storage medium. In some examples, memory 132 includes a temporary memory or a volatile memory. Examples of volatile memories include random access memories (RAM), dynamic random access memories (DRAM), static random access memories (SRAM), and other forms of volatile memories known in the art. Memory 132, in some examples, also includes one or more memories configured for long-term storage of information, e.g. including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

One or more input devices 134 of computing device 12 may receive input, e.g., from patient 4 or another user. Examples of input are tactile, audio, kinetic, and optical input. Input devices 134 may include, as examples, a mouse, keyboard, voice responsive system, camera, buttons, control pad, microphone, presence-sensitive or touch-sensitive component (e.g., screen), or any other device for detecting input from a user or a machine.

One or more output devices 136 of computing device 12 may generate output, e.g., to patient 4 or another user. Examples of output are tactile, audio, and visual output. Output devices 136 of computing device 12 may include a presence-sensitive screen, sound card, video graphics adapter card, speaker, cathode ray tube (CRT) monitor, liquid crystal display (LCD), light emitting diodes (LEDs), or any type of device for generating tactile, audio, and/or visual output.

One or more sensors 138 of computing device 12 may sense physiological parameters or signals of patient 4. Sensor(s) 138 may include electrodes, accelerometers (e.g., 3-axis accelerometers), one or more inertial measurement units (IMUs), an optical sensor, one or more impedance sensors, one or more temperature sensors, one or more pressure sensors, one or more heart sound sensors, and other sensors, and sensing circuitry (e.g., including an ADC), similar to those described above with respect to IMD 10 and FIG. 2. For instance, sensor(s) 138 may be configured to sense external physical state or internal physical state of patient 4.

Communication circuitry 140 of computing device 12 may communicate with other devices by transmitting and receiving data. Communication circuitry 140 may include a network interface card, such as an Ethernet card, an optical transceiver, a radio frequency transceiver, or any other type of device that can send and receive information. For example, communication circuitry 140 may include a radio transceiver configured for communication according to standards or protocols, such as 3G, 4G, 5G, WiFi (e.g., 802.11 or 802.15 ZigBee), Bluetooth®, or Bluetooth® Low Energy (BLE). For instance, communication circuitry 140 may include an antenna configured to wirelessly receive communication from a medical device (e.g., IMD 10). Processing circuitry 130 may be coupled to the antenna through communication circuitry 140.

As shown in FIG. 3, health monitoring application 150 executes in user space 102 of computing device 12. Health monitoring application 150 may be logically divided into presentation layer 152, application layer 154, and data layer 156. Presentation layer 152 may include a user interface (UI) component 160, which generates and renders user interfaces of health monitoring application 150.

Application layer 154 may include, but is not limited to, an event engine 170, rules engine 172, rules configuration component 174, event assistant 176, and location service 178. Event engine 170 may be responsive to receipt of an alert transmission from IMD 10 indicating that IMD 10 detected an acute health event. Event engine 170 may control performance of any of the operations in response to detection of an acute health event ascribed herein to computing device 12, such as activating an alarm, transmitting alert messages to HMS 22, controlling IoT devices 30, and analyzing data to confirm or override the detection of the acute health event by IMD 10.

Rules configuration component 174 analyzes sensed data 190, and in some examples, patient input 192 and/or EHR data 194, to determine whether there is a sufficient likelihood that patient 4 is experiencing the acute health event detected by IMD 10. Sensed data 190 may include data received from IMD 10 as part of the alert transmission, additional data transmitted from IMD 10, e.g., in "real-time," and physiological and other data related to the condition of patient 4 collected by computing device(s) 12 and/or IoT devices 30. For instance, the sensed data 190 may include data for one or more physical states. As examples sensed data 190 from computing device(s) 12 may include one or more of: activity levels, walking/running distance, resting energy, active energy, exercise minutes, quantifications of standing, body mass, body mass index, heart rate, low, high, and/or irregular heart rate events, heart rate variability, walking heart rate, heart beat series, digitized ECG, blood oxygen saturation, blood pressure (systolic and/or diastolic), respiratory rate, maximum volume of oxygen, blood glucose, peripheral perfusion, and sleep patterns. As additional examples, sensed data 190 may include data indicative of posture of patient 4, images of patient 4 captured in response to receiving message that patient 4 is experiencing an acute health event, voice recording of patient 4, or time-series of positioning information of patient 4, etc. For example, sensed data 190 may include image data, sounds captured by a microphone, posture data, and a time-series of positioning data of patient 4, as described in more detail.

As further examples, sensed data 190 includes an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern of patient 4. For instance, one or more sensors 58 (FIG. 2) or 138 may be a photoplethysmography, pulse oximetry, blood pressure, or external ECG sensors.

Patient input 192 may include responses to queries posed by health monitoring application 150 regarding the condition of patient 4, input by patient 4 or another user, such as bystander 26. The queries and responses may occur responsive to the detection of the event by IMD 10, or may have occurred prior to the detection, e.g., as part long-term monitoring of the health of patient 4. User recorded health data may include one or more of: exercise and activity data, sleep data, symptom data, medical history data, quality of life data, nutrition data, medication taking or compliance data, allergy data, demographic data, weight, and height. EHR data 194 may include any of the information regarding the historical condition or treatments of patient 4 described above. EHR data 194 may relate to history of cardiac arrest, tachyarrhythmia, myocardial infarction, stroke, seizure, chronic obstructive pulmonary disease (COPD), renal dysfunction, or hypertension, history of procedures, such as ablation or cardioversion, and healthcare utilization. EHR data 194 may also include demographic and other information of patient 4, such as age, gender, height, weight, and BMI.

Rules engine 172 may apply rules 196 to the data. Rules 196 may include one or more models, algorithms, decision trees, and/or thresholds. In some cases, rules 196 may be developed based on machine learning. In some examples, rules 196 and the operation of rules engine 172 may provide a more complex analysis of the sensed data received from IMD 10 or sensed by sensors 138, than is provided by rules engine 74 and rules 84. In some examples, rules 196 include one or more models developed by machine learning, and rules engine 172 applies feature vectors derived from the data to the model(s).

Rules configuration component 174 may be configured to modify rules 196 (and in some examples rules 84) based on feedback indicating whether the detections and confirmations of acute health events by IMD 10 and computing device 12 were accurate. The feedback may be received from patient 4, or from care providers 40 and/or EHR 24 via HMS 22. In some examples, rules configuration component 174 may utilize the data sets from true and false detections and confirmations for supervised machine learning to further train models included as part of rules 196.

As discussed above, event assistant 176 may provide a conversational interface for patient 4 and/or bystander 26 to exchange information with computing device 12. Event assistant 176 may query the user regarding the condition of patient 4 in response to receiving the alert message from IMD 10. Responses from the user may be included as patient input 192. Event assistant 176 may use natural language processing and context data to interpret utterances by the user. In some examples, in addition to receiving responses to queries posed by the assistant, event assistant 176 may be configured to respond to queries posed by the user. In some examples, event assistant 176 may provide directions to and respond to queries regarding treatment of patient 4 from patient 4 or bystander 26.

Location service 178 may determine the location of computing device 12 and, thereby, the presumed location of patient 4. Location service 178 may use global position system (GPS) data, multilateration, and/or any other known techniques for locating computing devices.

In some examples, processing circuitry 130 executes event engine 170 to confirm whether patient 4 is experiencing the acute health event. For instance, event engine 170 may utilize sensed data 190 to determine one or more physical states of patient 4. Event engine 170 may confirm whether patient 4 is experiencing or not experiencing the acute health event base don the determined one or more physical states. Event engine 170 may then output information based on the confirmation of whether the patient is experiencing or is not experiencing the acute health event.

For example, in response to the determination that the received communication indicates that 4 patient is experiencing an acute health event, event engine 170 may cause processing circuitry 130 to determine one or more physical states of the patient based on sensed data 190 from one or more sensors 138 or sensors 58. Examples of one or more sensors 138 include photoplethysmography, pulse oximetry, blood pressure, external ECG sensors, as well as accelerometers, inertial measurement units (IMUs), camera, or microphone. Processing circuitry 130 may store physical state data from sensors 138 as sensed data 190 in data layer 156.

As one example, the one or more physical states include one or more external physical states, and the one or more external physical states comprise one or more of a posture of patient 4, an eye opening of patient 4, a face color of patient 4, facial tone of patient 4, asymmetrical face or body response of patient 4, whether patient 4 is saying coherent words, and whether patient 4 fell down. As one example, the one or more physical states include one or more internal physical states, and the one or more internal physical states comprise one or more of an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern. In general, external physical states refer to physical states that can be determined by looking at patient 4, and internal physical states refer to physical states that cannot be determined by looking at patient 4. Although external and internal physical states are described based on ability to observe patient 4, the techniques do not require viewing of patient 4, expect of examples where images of patient 4 are taken. Rather by utilizing one or more sensors 138, event engine 170 may be configured to determine the one or more physical states of patient 4.

As one example, one or more sensors 138 include at least one of an accelerometer or inertial measurement unit (IMU), and the sensed data 190 includes information indicative of a posture of patient 4. To determine the one or more physical states of patient 4 based on sensed data 190 from one or more sensors 138, processing circuitry 130 (e.g., via event engine 170) is configured to determine whether patient 4 is in a vertical posture based on the information indicative of the posture of patient 4. As another example, one or more sensors 138 comprise at least one of an accelerometer or IMU, and the sensed data 190 includes information indicative of a time-series of positioning of patient 4. To determine the one or more physical states of patient 4 based on sensed data 190 from one or more sensors 138, processing circuitry 130 (e.g., via event engine 170) is configured to determine whether patient 4 fell based on the information indicative of the time-series of the positioning of patient 4.

As one example, one or more sensors 138 comprise a camera, and the sensed data 190 comprises an image of a face of patient 4 captured with the camera. To determine the one or more physical states of patient 4 based on sensed data 190 from one or more sensors 138, processing circuitry 130 (e.g., via event engine 170 and rules engine 172) may be configured to, at least one of, determine whether one or both eyes of patient 4 are open based on the image of the face, or determine a color of the face of patient 4. As an example, one or more sensors 138 comprises a microphone, and the sensed data 190 comprises information indicative of sound captured with the microphone. To determine the one or more physical states of patient 4 based on sensed data 190 from one or more sensors 138, processing circuitry 130 (e.g., via event engine 170) may be configured to determine whether patient 4 is in a physical state for providing sound based on the sound captured with the microphone.

As described above, the example components of computing device 12 shown in FIG. 3 may be similar to the components of IoT devices 30. For instance, IoT devices 30 may include the microphone and/or camera. Although the example techniques are described with respect to one or more computing devices 12, the example techniques may be performed by one or more computing devices 12 and/or one or more IoT devices 30. In some examples, one or more IoT devices 30 and one or more computing devices 12 may operate in concert. For instance, one or more IoT devices 30 may capture the images or record the sounds, and output the recorded sound and captured images to one or more computing devices 12 for processing. That is, sensed data 190 includes the images and sound captured by one or more IoT devices 30.

In some examples, processing circuitry 130 may be configured to determine physical state of patient 4 without relying on or in addition to relying on outputs from one or more sensors 138. For example, one or more sensors 58 of IMD 10 (FIG. 2) may be for sensing at least one of a cardiac signal, neurological signal, and respiratory signal, and processing circuitry 130 is configured to receive an instance of the communication from IMD 10 that includes information indicative of at least one of the cardiac signal, neurological signal, and respiratory signal. The information of the cardiac signal, neurological signal, and/or cardiac signal may be stored as sensed data 190. In such examples, to determine one or more physical states of patient 4 based on sensed data 190 from one or more sensors, processing circuitry 130 (e.g., via event engine 170) may be configured to determine a cardiac condition of patient 4 based on the information indicative of the cardiac signal, neurological signal, and/or cardiac signal.

Processing circuitry 130 may be configured to confirm that patient 4 is not experiencing the acute health event (e.g., SCA) based on the determined one or more physical states. For instance, processing circuitry 130 (e.g., via event engine 170) may utilize machine learning model(s) for the confirmation that patient 4 is not experiencing the acute health event (e.g., SCA). Use of machine learning model(s) is optional, and processing circuitry 130 may confirm that patient 4 is not experiencing the acute health event without utilizing artificial intelligence or machine learning techniques.

In some examples, if the one or more physical states indicate that the posture of patient 4 is vertical, the eye(s) of patient 4 are open, the face color of patient 4 is normal face color, patient 4 is able to state coherent words, and/or patient 4 did not fall down, processing circuitry 130 (e.g., via event engine 170) may confirm that that patient 4 is not experiencing the acute health event. Processing circuitry 130 may similarly use data of one or more internal physical states to confirm that patient 4 is or is not experiencing the acute health event.

Processing circuitry 130 (e.g., via event engine 170) may output information based on the confirmation that patient 4 is not experiencing the acute health event. For example, as described above, there may be benefit in deprioritizing an alert if confirmed that patient 4 is not experiencing the acute health event. Processing circuitry 130 may output instructions to cease an output of an alert, prevent the output of the alert, or delay the output of the alert. As another example, processing circuitry 130 may be configured to cause at least one of the medical device (e.g., IMD 10) or computing device 12A or 12B to output information to an emergency response system (e.g., EMS) indicating that the patient is not experiencing the acute health event.

For instance, if the alert was already outputted, by ceasing the alert and indicating that medical services are not needed, resources may be saved by avoiding unnecessary care. If the alert does not need to be outputted, by preventing the alert, unnecessary calls to emergency services can be avoided. In some cases, there may be benefits in waiting until there is additional confirmation of whether patient 4 is experiencing the acute health event. In such cases, rather than ceasing or preventing the alert, there may be benefits in delaying the alert until additional confirmation can be made.

Processing circuitry 130 may execute location service 178 to determine the location of computing device 12 and, thereby, the presumed location of patient 4. Processing circuitry 130 may use global position system (GPS) data, multilateration, and/or any other known techniques for locating computing devices. In some examples, event engine 170 may use the location of patient 4 and geofence data to determine an alert area as a geofence area.

For example, processing circuitry 130 may utilize the geofence area to determine if patient 4 is receiving medical services. Based on the geofence area, processing circuitry 130 may determine that patient 4 is proximate to or inside a hospital. If communication between computing device 12A or 12B and HMS 22 is within the geofence area (e.g., based on HMS 22 outputting its GPS location), processing circuitry 130 may determine that patient 4 is receiving medical services. In examples where processing circuitry 130 determines that medical services are being provided to patient 4, processing circuitry 130 may at least one of cease, prevent, or delay output of an alert.

Figure 4:
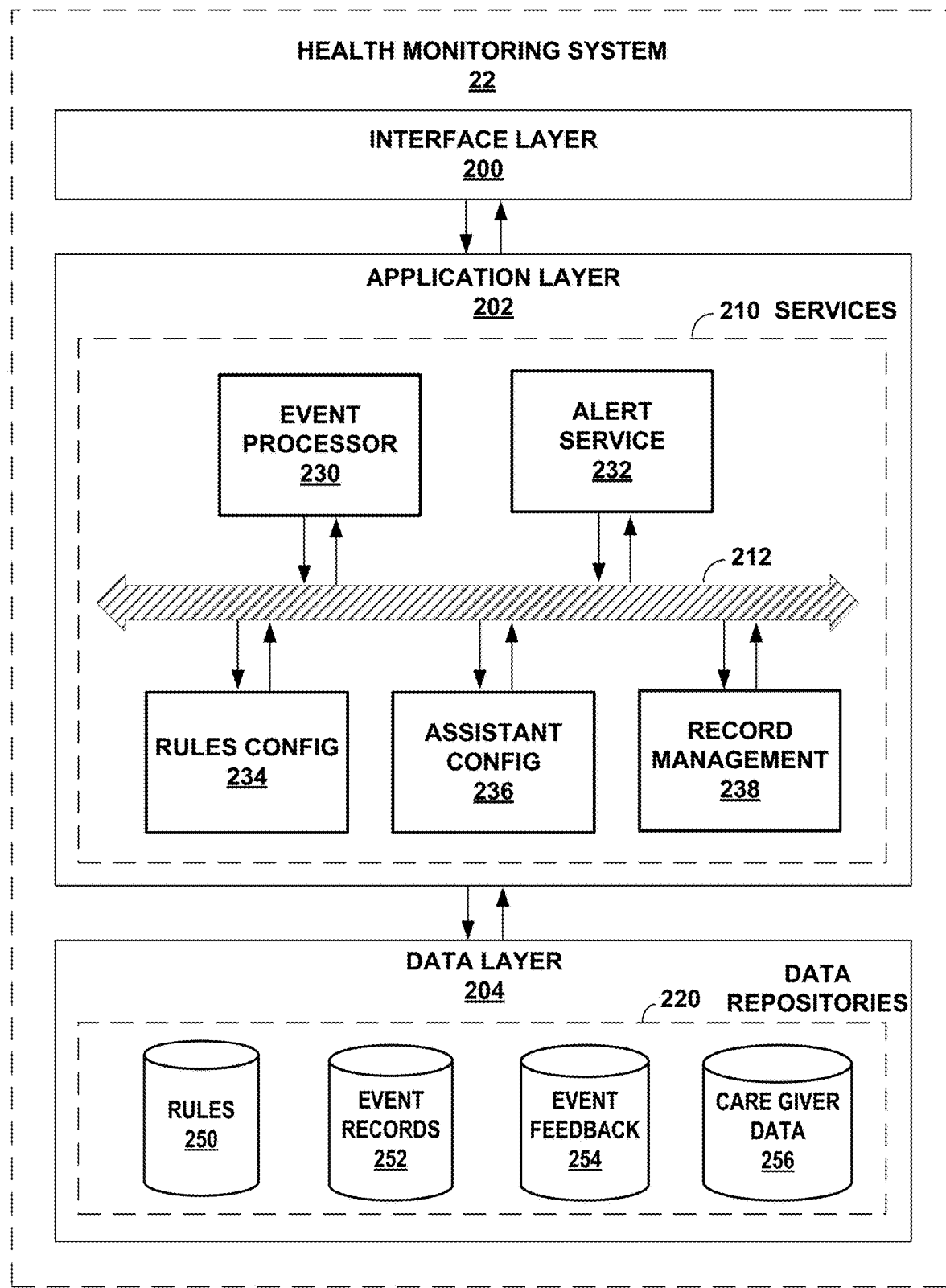
FIG. 4 is a block diagram illustrating an example configuration of a health monitoring system that operates in accordance with one or more techniques of the present disclosure.

FIG. 4 is a block diagram illustrating an operating perspective of HMS 22. HMS 22 may be implemented in a computing system 20, which may include hardware components such as those of computing device 12, embodied in one or more physical devices. FIG. 4 provides an operating perspective of HMS 22 when hosted as a cloud-based platform. In the example of FIG. 4, components of HMS 22 are arranged according to multiple logical layers that implement the techniques of this disclosure. Each layer may be implemented by one or more modules comprised of hardware, software, or a combination of hardware and software.

Computing devices, such as computing devices 12, IoT devices 30, computing devices 38, and computing device 42, operate as clients that communicate with HMS 22 via interface layer 200. The computing devices typically execute client software applications, such as desktop application, mobile application, and web applications. Interface layer 200 represents a set of application programming interfaces (API) or protocol interfaces presented and supported by HMS 22 for the client software applications. Interface layer 200 may be implemented with one or more web servers.

As shown in FIG. 4, HMS 22 also includes an application layer 202 that represents a collection of services 210 for implementing the functionality ascribed to HMS herein. Application layer 202 receives information from client applications, e.g., an alert of an acute health event from a computing device 12 or IoT device 30, and further processes the information according to one or more of the services 210 to respond to the information. Application layer 202 may be implemented as one or more discrete software services 210 executing on one or more application servers, e.g., physical or virtual machines. That is, the application servers provide runtime environments for execution of services 210. In some examples, the functionality interface layer 200 as described above and the functionality of application layer 202 may be implemented at the same server. Services 210 may communicate via a logical service bus 212. Service bus 212 generally represents a logical interconnections or set of interfaces that allows different services 210 to send messages to other services, such as by a publish/subscription communication model.

Data layer 204 of HMS 22 provides persistence for information in PPEMS 6 using one or more data repositories 220. A data repository 220, generally, may be any data structure or software that stores and/or manages data. Examples of data repositories 220 include but are not limited to relational databases, multi-dimensional databases, maps, and hash tables, to name only a few examples.

As shown in FIG. 4, each of services 230-238 is implemented in a modular form within HMS 22. Although shown as separate modules for each service, in some examples the functionality of two or more services may be combined into a single module or component. Each of services 230-238 may be implemented in software, hardware, or a combination of hardware and software. Moreover, services 230-238 may be implemented as standalone devices, separate virtual machines or containers, processes, threads or software instructions generally for execution on one or more physical processors.

Event processor service 230 may be responsive to receipt of an alert transmission from computing device(s) 12 and/or IoT device(s) 30 indicating that IMD 10 detected an acute health event of patient and, in some examples, that the transmitting device confirmed the detection. Event processor service 230 may initiate performance of any of the operations in response to detection of an acute health event ascribed herein to HMS 22, such as communicating with patient 4, bystander 26, and care providers 40, activating drone 46 and, in some cases, analyzing data to confirm or override the detection of the acute health event by IMD 10.

Record management service 238 may store the patient data included in a received alert message within event records 252. Alert service 232 may package the some or all of the data from the event record, in some cases with additional information as described herein, into one more alert messages for transmission to bystander 26 and/or care providers 40. Care giver data 256 may store data used by alert service 232 to identify to whom to send alerts based on locations of potential bystanders 26 and care providers 40 relative to a location of patient 4 and/or applicability of the care provided by care providers 40 to the acute health event experienced by patient 4.

In examples in which HMS 22 performs an analysis to confirm or override the detection of the acute health event by IMD 10, event processor service 230 may apply one or more rules 250 to the data received in the alert message, e.g., to feature vectors derived by event processor service 230 from the data. Rules 250 may include one or more models, algorithms, decision trees, and/or thresholds, which may be developed by rules configuration service 234 based on machine learning. Example machine learning techniques that may be employed to generate rules 250 can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LS™), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, in addition to rules used by HMS 22 to confirm acute health event detection, (or in examples in which HMS 22 does not confirm event detection) rules 250 maintained by HMS 22 may include rules 196 utilized by computing devices 12 and rules 84 used by IMD 10. In such examples, rules configuration service 250 may be configured to develop and maintain rules 196 and rules 84. Rules configuration service 234 may be configured to modify these rules based on event feedback data 254 that indicates whether the detections and confirmations of acute health events by IMD 10, computing device 12, and/or HMS 22 were accurate. Event feedback 254 may be received from patient 4, e.g., via computing device(s) 12, or from care providers 40 and/or EHR 24. In some examples, rules configuration service 234 may utilize event records from true and false detections (as indicated by event feedback data 254) and confirmations for supervised machine learning to further train models included as part of rules 250.

As illustrated in the example of FIG. 4, services 210 may also include an assistant configuration service 236 for configuring and interacting with event assistant 176 implemented in computing device 12 or other computing devices.

Figure 5:
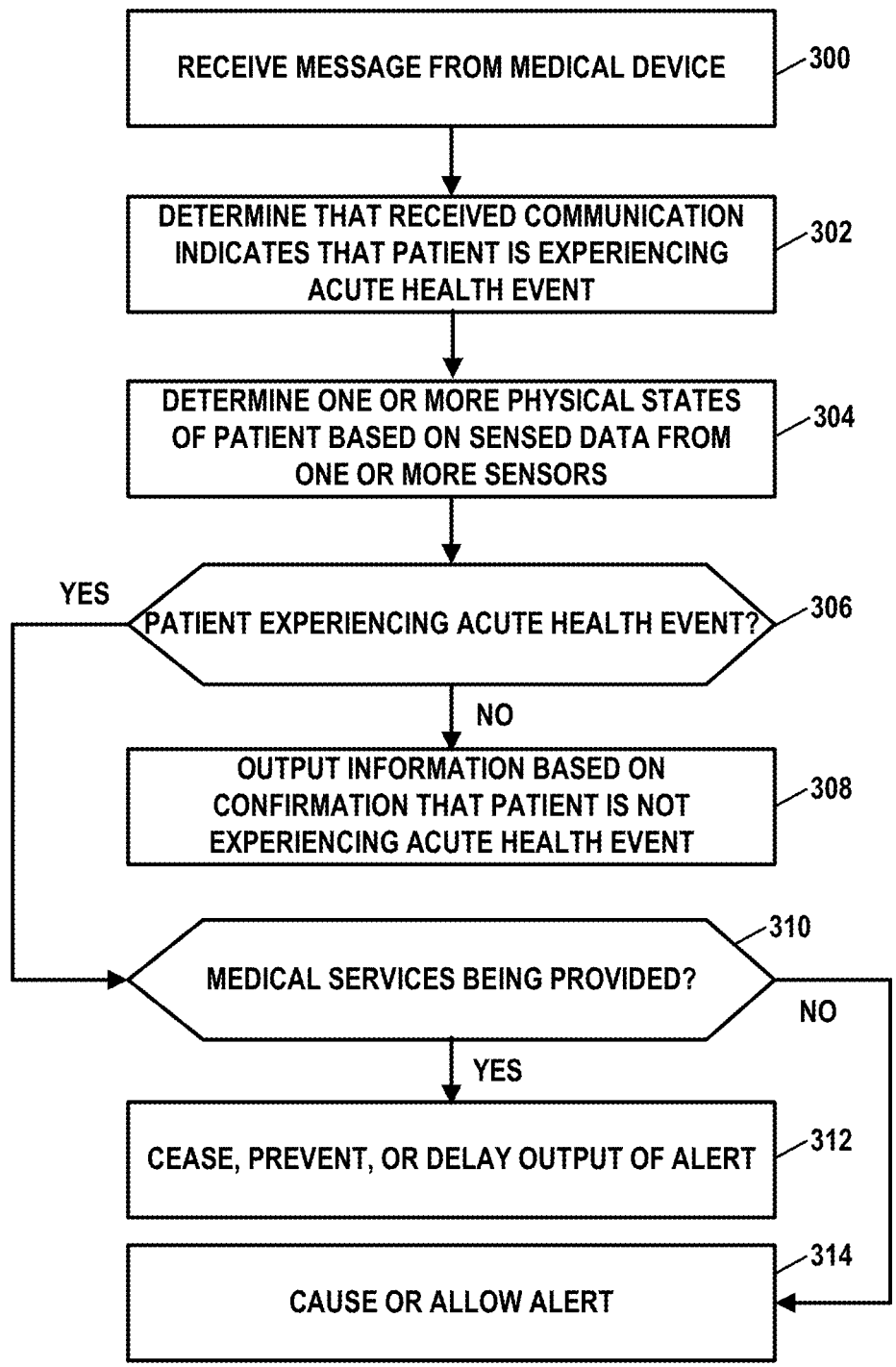
FIG. 5 is a flow diagram illustrating an example technique for providing automatic alert control for an acute health event of a patient.

FIG. 5 is a flow diagram illustrating an example technique for providing automatic alert control for an acute health event of a patient (e.g., a method of acute health event confirmation). The example technique of FIG. 5 is described as being implemented by processing circuitry 130 of computing device 12. However, the example techniques may be performed by a device such as one or more computing devices 12, computing device 42, one or more computing devices 38, and one or more IoT devices 30, or a combination of one or more computing devices 12 and one or more IoT devices 30. Therefore, although the description of the operation is with respect to processing circuitry 130, the example techniques may be performed with processing circuitry from any one or combination of one or more computing devices 12, computing device 42, one or more computing devices 38, and one or more IoT devices 30. Accordingly, the term "computing device" or simply "device" encompasses examples of one or more computing devices 12, computing device 42, one or more computing devices 38, and one or more IoT devices 30, or any combination of one or more computing devices 12, computing device 42, one or more computing devices 38, and one or more IoT devices 30.

Moreover, in some examples, the processing circuitry that performs the example techniques of this disclosure may be processing circuitry 130 or a combination of processing circuitry of various devices (e.g., one or more computing devices 12 and/or one or more IoT devices 30, or other devices illustrated in FIG. 1). Accordingly, the example techniques described in this disclosure may be considered as being performed by one or more devices of a patient. Examples of the one or more devices includes one or any combination of one or more computing devices 12, one or more IoT devices 30, or other devices illustrated in FIG. 1. For ease, the example of FIG. 5 is described with respect to processing circuitry 130 and computing device 12.

According to the example illustrated by FIG. 5, the antenna of communication circuitry 140 wirelessly receives communication from a medical device (e.g., IMD 10) (300). Processing circuitry 130, coupled to the antenna through communication circuitry 140, may determine that the received communication indicates that patient 4 is experiencing an acute health event (e.g., SCA) (302).

In response to the determination that the received communication indicates that patient 4 is experiencing the acute health event, processing circuitry 130 may determine one or more physical states of patient 4 based on sensed data from one or more sensors (304). In some examples, processing circuitry 130 may perform the example techniques based on confidence in the determination by the medical device that patient 4 is experiencing the acute health event. As one example, if the medical device further outputs communication indicating high confidence that patient 4 is experiencing the acute health event, then processing circuitry 130 may bypass the example techniques and cause an alert to be output. However, if the medical device further outputs communication indicating low confidence that patient 4 is experiencing the acute health event, then processing circuitry 130 may perform the example techniques to confirm whether patient 4 is experiencing the acute health event.

Examples of the one or more sensors include sensors 138, but the one or more sensors need not necessarily be sensors 138 and may be sensors 58 of IMD 10. One or more sensors 138 may store the sensed data as sensed data 190, and processing circuitry 130 may store the sensed data received from sensors 58 also as sensed data 190.

In one or more examples, processing circuitry 130 may execute event engine 170. In response to the execution of event engine 170, event engine 170 may cause processing circuitry 130 to access sensed data 190 to determine one or more physical states of patient 4. Examples of the one or more physical states include external physical states such as posture of patient 4, eye opening of patient 4, face color of patient 4, and whether patient 4 fell, or internal physical states such as an electrocardiogram, an intracardiac or intrathoracic impedance, a respiration rate, a heart sound, a pulse, an oxygenation level, change in blood volume, a blood pressure, change in cardiac rhythm, change in cardiac rate, or change in cardiac conduction pattern.

As described above, there may be various ways in which processing circuitry 130 may determine one or more physical states of patient 4 based on sensed data 190 from one or more sensors (e.g., sensors 138, 58, or other sensors). The following are a few examples that may be utilized separately or in combination.

One or more sensors 138 (e.g., of computing device 12 or IoT device 30) may include a camera, and the sensed data may include an image of a face of patient 4 captured with the camera. To determine one or more physical states, processing circuitry 130 may be configured to, at least one of, determine whether one or both eyes of the patient are open based on the image of the face, or determine a color of the face of the patient.

One or more sensors 138 may include at least one of an accelerometer or IMU, and the sensed data may include information indicative of a posture of patient 4. To determine the one or more physical states, processing circuitry 130 may be configured to determine whether patient 4 is in a vertical posture based on the information indicative of the posture of patient 4.

One or more sensors 138 may include at least one of an accelerometer or IMU, and the sensed data may include information indicative of a time-series of positioning of patient 4. To determine the one or more physical states, processing circuitry 130 may be configured to determine whether patient 4 fell based on the information indicative of the time-series of the positioning of patient 4.

One or more sensors 138 (e.g., of computing device 12 or IoT device 30) may include a microphone, and the sensed data may include information indicative of sound captured with the microphone. To determine the one or more physical states, processing circuitry 130 may be configured to determine whether patient 4 is in a physical state for providing sound based on the sound captured with the microphone.

The one or more sensors may include one or more sensors 58 of the medical device (e.g., IMD 10) for sensing at least one of a cardiac signal, neurological signal, and respiratory signal. To determine one or more physical states of patient 4 based on sensed data from one or more sensors 58, processing circuitry 130 may be configured to determine a cardiac condition of patient 4 based on the information indicative of the cardiac signal, neurological signal, and/or respiratory signal.

For example, processing circuitry 130 may receive information of the cardiac signal, neurological signal, and/or respiratory signal that IMD 10 used to determine that patient 4 was experiencing an acute health event. Processing circuitry 130 may be configured to determine the cardiac condition of patient 4 based on the information of the cardiac signal, neurological signal, and/or respiratory signal that IMD 10 used to determine that patient 4 was experiencing the acute health event (e.g., confirm that IMD 10 correctly determined that patient 4 is experiencing the acute cardiac event).

As another example, IMD 10 may output a subsequent cardiac signal, neurological signal, and/or cardiac signal that processing circuitry 130 receives. Processing circuitry 130 may determine if the acute health event is no longer occurring. For example, processing circuitry 130 receives new ECG waveforms (e.g., which are examples of a cardiac signal) from IMD 10 and determines through post-processing that the acute health event (e.g., SCA) is no longer happening. In this example, processing circuit 130 may determine a cardiac condition of patient 4 based on the subsequent cardiac signal that indicates whether the acute health even is still happening or not. The time between when processing circuitry 130 receives the first cardiac signal and the subsequent cardiac signal may be a few seconds (e.g., less than 1 minute, less than 30 seconds, less than 10 seconds, less than 5 seconds, or less than 2 seconds). Processing circuitry 130 may perform similar operations for neurological signal and/or respiratory signal.

Processing circuitry 130 may confirm whether patient 4 is experiencing an acute health event based on the determined one or more physical states (306). For instance, if the posture of patient 4 is vertical, then processing circuitry 130 may confirm that patient 4 is not experiencing the acute health event. If the eyes of patient 4 are open or the face color of patient 4 is normal, then processing circuitry 130 may confirm that patient 4 is not experiencing the acute health event. If patient 4 did not fall (e.g., based on the time-series of positioning of patient 4), then processing circuitry 130 may confirm that patient 4 is not experiencing the acute health event. If patient 4 made sounds that form coherent words (e.g., saying "I'm okay"), as captured by the microphone, then processing circuitry 130 may confirm that patient 4 is not experiencing the acute health event. If the cardiac signal, received from IMD 10, indicates that the heartbeat of patient 4 is normal or at least not indicative of the acute health event, processing circuitry 130 may confirm that patient 4 is not experiencing the acute health event.

In some examples, to confirm whether patient 4 is experiencing the acute health event, processing circuitry 130 may output a request for patient feedback. Processing circuitry 130 may confirm that patient 4 is not experiencing the acute health event based on the determination of the one or more physical states and based on reception of the patient feedback responsive to the request for patient feedback. Examples of the patient feedback may be a particular tapping sequence (e.g., on the body near IMD 10 or on computing device 12A or 12B), a wave of the arm, a verbal reply, and the like (e.g., some action that indicates that the patient 4 is conscious and voluntarily making the movements).

If processing circuitry 130 confirms that patient 4 is not experiencing the acute health event ("NO" of 306), processing circuitry 130 may output information based on the confirmation that patient 4 is not experiencing the acute health event (308). For example, processing circuitry 130 may be configured to output instructions to cease an output of an alert, prevent the output of the alert, or delay the output of the alert. As another example, processing circuitry 130 may be configured to cause at least one of the medical device (e.g., IMD 10) or computing device 12A or 12B to output information to an emergency response system (e.g., EMS) indicating that patient 4 is not experiencing the acute health event.

If processing circuitry 130 confirms that patient 4 is experiencing the acute health event ("YES" of 306), processing circuitry 130 may determine whether medical services are being provided (310). For instance, processing circuitry 130 may utilize geofence data and location service 178 to determine whether patient 4 is at a hospital or with emergency services.

If determined that medical services are being provided ("YES" of 310), processing circuitry 130 may cease, prevent, or delay output of the alert notification (312). For example, once EMS is on the job to provide medical services, retriggering alerts/dialing 911 may be avoided. If determined that medical services are not being provided ("NO" of 310), processing circuitry 130 may cause or allow the output of the alert (314).

The following describes some example clauses of techniques described in this disclosure. The example clauses may be performed separately or together in any combination.

Clause 1: A device of a patient includes an antenna configured to wirelessly receive communication from a medical device; and processing circuitry coupled to the antenna and configured to: determine that the received communication indicates that a patient is experiencing an acute health event; in response to the determination, determine one or more physical states of the patient based on sensed data from one or more sensors; confirm that the patient is not experiencing the acute health event based on the determined one or more physical states; and output information based on the confirmation that the patient is not experiencing the acute health event.

Clause 2: The device of clause 1, wherein to output the information, the processing circuitry is configured to output instructions to cease an output of an alert, prevent the output of the alert, or delay the output of the alert.

Clause 3: The device of any of clauses 1 and 2, wherein to output the information, the processing circuitry is configured to cause at least one of the medical device or the device to output information to an emergency response system indicating that the patient is not experiencing the acute health event.

Clause 4: The device of any of clauses 1 through 3, wherein the one or more physical states include one or more external physical states, and wherein the one or more external physical states comprise one or more of: a posture of the patient; an eye opening; a face color; facial tone; or asymmetrical face or body response.

Clause 5: The device of any of clauses 1 through 4, wherein the one or more physical states include one or more internal physical states, and wherein the one or more internal physical states comprise one or more of: an electrocardiogram; an intracardiac or intrathoracic impedance; a respiration rate; a heart sound; a pulse; an oxygenation level; change in blood volume; a blood pressure; change in cardiac rhythm; change in cardiac rate; or change in cardiac conduction pattern.

Clause 6: The device of any of clauses 1 through 5, wherein the device includes the one or more sensors.

Clause 7: The device of any of clauses 1 through 6, wherein the one or more sensors comprise a camera of the device, wherein the sensed data comprises an image of a face of the patient captured with the camera, and wherein to determine the one or more physical states of the patient based on sensed data from one or more sensors, the processing circuitry is configured to, at least one of, determine whether one or both eyes of the patient are open based on the image of the face, or determine a color of the face of the patient.

Clause 8: The device of any of clauses 1 through 7, wherein the one or more sensors comprise at least one of an accelerometer or inertial measurement unit (IMU) of the device, wherein the sensed data comprises information indicative of a posture of the patient, and wherein to determine the one or more physical states of the patient based on sensed data from one or more sensors, the processing circuitry is configured to determine whether the patient is in a vertical posture based on the information indicative of the posture of the patient.

Clause 9: The device of any of clauses 1 through 8, wherein the one or more sensors comprise at least one of an accelerometer or inertial measurement unit (IMU) of the device, wherein the sensed data comprises information indicative of a time-series of positioning of the patient, and wherein to determine the one or more physical states of the patient based on sensed data from one or more sensors, the processing circuitry is configured to determine whether the patient fell based on the information indicative of the time-series of the positioning of the patient.

Clause 10: The device of any of clauses 1 through 9, wherein the one or more sensors comprises a microphone of the device, wherein the sensed data comprises information indicative of sound captured with the microphone, and wherein to determine the one or more physical states of the patient based on sensed data from one or more sensors, the processing circuitry is configured to determine whether the patient is in a physical state for providing sound based on the sound captured with the microphone.

Clause 11: The device of any of clauses 1 through 10, wherein the one or more sensors comprise one or more sensors of the medical device for sensing at least one of a cardiac signal, a neurological signal, and a respiratory signal, wherein the received communication that indicates that the patient is experiencing the acute health event comprises a first instance of the communication, wherein the processing circuitry is configured to receive a second instance of the communication that includes information indicative of at least one of the cardiac signal, the neurological signal, and the respiratory signal, and wherein to determine one or more physical states of the patient based on sensed data from one or more sensors, the processing circuitry is configured to determine a cardiac condition of the patient based on the information indicative of at least one of the cardiac signal, the neurological signal, and the respiratory signal.

Clause 12: The device of any of clauses 1 through 11, wherein the processing circuitry is configured to output a request for patient feedback, and wherein to confirm that the patient is not experiencing the acute health event, the processing circuitry is configured to confirm that the patient is not experiencing the acute health event based on the determination of the one or more physical states and based on reception of the patient feedback responsive to the request for patient feedback.

Clause 13: The device of any of clauses 1 through 12, wherein the communication is a first instance of the communication, wherein the determination that the received communication indicates that the patient is experiencing the acute health event comprises a determination, in a first instance, that the received communication indicates that the patient is experiencing the acute health event, and wherein the processing circuitry is configured to: determine, in a second instance, that a second instance of the communication indicates that the patient is experiencing the acute health event; determine, in the second instance, that medical services are being provided to the patient; and at least one of cease, prevent, or delay output of an alert.

Clause 14: The device of any of clauses 1 through 13, wherein the device of the patient comprises at least one of a smartphone, a smartwatch, a wearable ring, wearable health sensor, smart clothing, or an Internet of Things (IoT) device.

Clause 15: The device of any of clauses 1 through 14, wherein the acute health event is a sudden cardiac arrest (SCA).

Clause 16: A method of acute health event confirmation, the method includes receiving, with one or more devices of a patient, communication from a medical device; determining, with the one or more devices of the patient, that the received communication indicates that the patient is experiencing an acute health event; in response to the determination, determining, with the one or more devices of the patient, one or more physical states of the patient based on sensed data from one or more sensors; confirming, with the one or more devices of the patient, that the patient is not experiencing the acute health event based on the determined one or more physical states; and outputting, with the one or more devices, information based on the confirmation that the patient is not experiencing the acute health event.

Clause 17: The method of clause 16, wherein outputting the information comprises outputting instructions to cease an output of an alert, prevent the output of the alert, or delay the output of the alert.

Clause 18: The method of any of clauses 16 and 17, wherein outputting the information comprises cause at least one of the medical device or the one or more devices to output information to an emergency response system indicating that the patient is not experiencing the acute health event.

Clause 19: The method of any of clauses 16 through 18, wherein the one or more physical states include one or more external physical states, and wherein the one or more external physical states comprise one or more of: a posture of the patient; an eye opening; a face color; facial tone; or asymmetrical face or body response.

Clause 20: The method of any of clauses 16 through 19, wherein the one or more physical states include one or more internal physical states, and wherein the one or more internal physical states comprise one or more of: an electrocardiogram; an intracardiac or intrathoracic impedance; a respiration rate; a heart sound; a pulse; an oxygenation level; change in blood volume; a blood pressure; change in cardiac rhythm; change in cardiac rate; or change in cardiac conduction pattern.

Clause 21: The method of any of clauses 16 through 20, wherein the one or more sensors comprise a camera of the one or more devices, wherein the sensed data comprises an image of a face of the patient captured with the camera, and wherein determining the one or more physical states of the patient based on sensed data from one or more sensors comprises at least one of determining whether one or both eyes of the patient are open based on the image of the face, or determining a color of the face of the patient.

Clause 22: The method of any of clauses 16 through 21, wherein the one or more sensors comprise at least one of an accelerometer or inertial measurement unit (IMU) of the one or more devices, wherein the sensed data comprises information indicative of a posture of the patient, and wherein determining the one or more physical states of the patient based on sensed data from one or more sensors comprises determining whether the patient is in a vertical posture based on the information indicative of the posture of the patient.

Clause 23: The method of any of clauses 16 through 22, wherein the one or more sensors comprise at least one of an accelerometer or inertial measurement unit (IMU) of the one or more devices, wherein the sensed data comprises information indicative of a time-series of positioning of the patient, and wherein determining the one or more physical states of the patient based on sensed data from one or more sensors comprises determining whether the patient fell based on the information indicative of the time-series of the positioning of the patient.

Clause 24: The method of any of clauses 16 through 23, wherein the one or more sensors comprises a microphone of the one or more devices, wherein the sensed data comprises information indicative of sound captured with the microphone, and wherein determining the one or more physical states of the patient based on sensed data from one or more sensors comprises determining whether the patient is in a physical state for providing sound based on the sound captured with the microphone.

Clause 25: The method of any of clauses 16 through 24, wherein the one or more sensors comprise one or more sensors of the medical device for sensing at least one of a cardiac signal, a neurological signal, and a respiratory signal, wherein the received communication that indicates that the patient is experiencing the acute health event comprises a first instance of the communication, the method further comprising receiving a second instance of the communication that includes information indicative of at least one of the cardiac signal, the neurological signal, and the respiratory signal, and wherein determining one or more physical states of the patient based on sensed data from one or more sensors comprises determining a cardiac condition of the patient based on the information indicative of at least one of the cardiac signal, the neurological signal, and the respiratory signal.

Clause 26: The method of any of clauses 16 through 25, further comprising outputting a request for patient feedback, wherein confirming that the patient is not experiencing the acute health event comprises confirming that the patient is not experiencing the acute health event based on the determination of the one or more physical states and based on reception of the patient feedback responsive to the request for patient feedback.

Clause 27: The method of any of clauses 16 through 26, wherein the communication is a first instance of the communication, wherein the determination that the received communication indicates that the patient is experiencing the acute health event comprises a determination, in a first instance, that the received communication indicates that the patient is experiencing the acute health event, the method further includes determining, in a second instance, that a second instance of the communication indicates that the patient is experiencing the acute health event; determining, in the second instance, that medical services are being provided to the patient; and at least one of ceasing, preventing, or delaying output of an alert.

Clause 28: The method of any of clauses 16 through 27, wherein the one or more devices of the patient comprise at least one of a smartphone, a smartwatch, a wearable ring, wearable health sensor, smart clothing, or an Internet of Things (IoT) device.

Clause 29: The method of any of clauses 16 through 28, wherein the acute health event is a sudden cardiac arrest (SCA).

Clause 30: A computer-readable storage medium storing instructions thereon that when executed cause one or more processors to: determine that received communication from a medical device indicates that a patient is experiencing an acute health event; in response to the determination, determine one or more physical states of the patient based on sensed data from one or more sensors; confirm that the patient is not experiencing the acute health event based on the determined one or more physical states; and output information based on the confirmation that the patient is not experiencing the acute health event.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A system comprising:
   an implantable cardiac monitoring device configured to:
      determine that a patient is experiencing a sudden cardiac arrest based on sensing by the implantable cardiac monitoring device within the patient; and
      transmit a first communication that indicates that the patient is experiencing the sudden cardiac arrest; and
   one or more devices of the patient that are different than the implantable cardiac monitoring device, the one or more devices comprising processing circuitry configured to:
      determine, based at least in part on the first communication received from the implantable cardiac monitoring device, that the implantable cardiac monitoring device has determined that the patient is experiencing the sudden cardiac arrest;
      initiate a request to facilitate delivery of care that is to be provided by one or more care providers or bystanders for medical services to the patient in response to the determination that the implantable cardiac monitoring device has determined that the patient is experiencing the sudden cardiac arrest;
      subsequent to initiating the request, confirm that the patient is not experiencing the sudden cardiac arrest based at least in part on a second communication received from the implantable cardiac monitoring device, wherein the second communication received from the implantable cardiac monitoring device is different than the first communication, and wherein the second communication received from the implantable cardiac monitoring device includes at least one of: (1) information from the implantable cardiac monitoring device indicating that the patient is not experiencing the sudden cardiac arrest, or (2) data sensed by the implantable cardiac monitoring device from which the processing circuitry can confirm that the patient is not experiencing the sudden cardiac arrest; and
      in response to the confirmation, output information to cause a change in the request for the medical services to one or more of the same one or more care providers or bystanders.

2. The system of claim 1, wherein the request to facilitate delivery of care comprises a higher-level priority request, and wherein to output the information to cause the change in the request for the medical services, the processing circuitry is configured to output instructions to cease the output of the higher-level priority request and output a lower-level priority request, wherein the lower-level priority request requires fewer medical services as compared to the higher-level priority request.

3. The system of claim 1, wherein to output the information to cause the change in the request for the medical services, the processing circuitry is configured to cause the one or more devices to output information for an emergency response system of the one or more care providers indicating that the patient is not experiencing the sudden cardiac arrest.

4. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more physical states include one or more external physical states, and wherein the one or more external physical states comprise one or more of:
   a posture of the patient;
   an eye opening;
   a face color;
   facial tone; or
   asymmetrical face or body response.

5. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more physical states include one or more internal physical states, and wherein the one or more internal physical states comprise one or more of:
   an electrocardiogram;
   an intracardiac or intrathoracic impedance;
   a respiration rate;
   a heart sound;
   a pulse;
   an oxygenation level;
   change in blood volume;
   a blood pressure;
   change in cardiac rhythm;
   change in cardiac rate; or
   change in cardiac conduction pattern.

6. The system of claim 1, wherein the one or more devices include one or more sensors.

7. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more sensors comprise a camera of the one or more devices, wherein the sensed data comprises an image of a face of the patient captured with the camera, and wherein to determine the one or more physical states of the patient based on sensed data from one or more sensors, the processing circuitry is configured to, at least one of, determine whether one or both eyes of the patient are open based on the image of the face, or determine a color of the face of the patient.

8. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more sensors comprise at least one of an accelerometer or inertial measurement unit (IMU) of the one or more devices, wherein the sensed data comprises information indicative of a posture of the patient, and wherein to determine the one or more physical states of the patient based on sensed data from one or more sensors, the processing circuitry is configured to determine whether the patient is in a vertical posture based on the information indicative of the posture of the patient.

9. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more sensors comprise at least one of an accelerometer or inertial measurement unit (IMU) of the one or more devices, wherein the sensed data comprises information indicative of a time-series of positioning of the patient, and wherein to determine the one or more physical states of the patient based on sensed data from one or more sensors, the processing circuitry is configured to determine whether the patient fell based on the information indicative of the time-series of the positioning of the patient.

10. The system of claim 1, wherein the processing circuitry is configured to confirm that the patient is not experiencing the sudden cardiac arrest also based on one or more physical states of the patient, wherein the processing circuitry is configured to determine the one or more physical states of the patient based on sensed data from one or more sensors, wherein the one or more sensors comprises a microphone of the one or more devices, wherein the sensed data comprises information indicative of sound captured with the microphone, and wherein to determine the one or more physical states of the patient based on sensed data from one or more sensors, the processing circuitry is configured to determine whether the patient is in a physical state for providing sound based on the sound captured with the microphone.

11. The system of claim 1, wherein the data sensed by the implantable cardiac monitoring device from which the processing circuitry can confirm that the patient is not experiencing the sudden cardiac arrest comprises data for at least one of a cardiac signal, a neurological signal, and a respiratory signal.

12. The system of claim 1, wherein the processing circuitry is configured to output a request for patient feedback via the one or more devices, and wherein to confirm that the patient is not experiencing the sudden cardiac arrest, the processing circuitry is configured to confirm that the patient is not experiencing the sudden cardiac arrest also based on reception of the patient feedback responsive to the request for patient feedback.

13. The system of claim 1, wherein the determination that the implantable cardiac monitoring device has determined that the patient is experiencing the sudden cardiac arrest comprises a determination, in a first instance, that the implantable cardiac monitoring device has determined that the patient is experiencing the sudden cardiac arrest, and wherein the processing circuitry is configured to:
determine, in a second instance, based at least in part on a third communication received from the implantable cardiac monitoring device, that the implantable cardiac monitoring device has determined that the patient is experiencing the sudden cardiac arrest;
determine, in the second instance, that medical services are being provided to the patient; and
at least one of cease, prevent, or delay output of an alert.

14. The system of claim 1, wherein at least one of the one or more devices of the patient comprises at least one of a smartphone, a smartwatch, a wearable ring, wearable health sensor, smart clothing, or an Internet of Things (IoT) device, and the sudden cardiac arrest is a sudden cardiac arrest (SCA).

15. The system of claim 1, wherein the information comprises a message that further includes ceasing the request to facilitate the delivery of care.

16. The system of claim 1, wherein to output the information to cause the change, the processing circuitry is configured to output the information without user intervention.

17. The system of claim 1, further comprising a cloud-based platform, wherein to confirm that the patient is not experiencing the sudden cardiac arrest, the processing circuitry is configured to confirm that the patient is not experiencing the sudden cardiac arrest also based on processing in the cloud-based platform.

18. The system of claim 1,
wherein the one or more devices comprises at least a first device and a second device,
wherein the processing circuitry comprises a first set of processing circuitry of the first device and a second set of processing circuitry of the second device,
wherein to determine that the implantable cardiac monitoring device has determined that the patient is experiencing the sudden cardiac arrest, the first set of processing circuitry of the first device is configured to determine that the implantable cardiac monitoring device determined that the patient is experiencing the sudden cardiac arrest, and
wherein to confirm that the patient is not experiencing the sudden cardiac arrest, the second set of processing circuitry of the second device is configured to confirm that the patient is not experiencing the sudden cardiac arrest.

19. A method of sudden cardiac arrest confirmation, the method comprising:
determining, with an implantable cardiac monitoring device, that a patient is experiencing a sudden cardiac arrest based on sensing by the implantable cardiac monitoring device within the patient;
transmitting, with the implantable cardiac monitoring device, a first communication that indicates that the patient is experiencing the sudden cardiac arrest;
determining, with one or more devices of the patient that are different than the implantable cardiac monitoring device, based at least in part on the first communication received from the implantable cardiac monitoring device, that the implantable cardiac monitoring device has determined that the patient is experiencing the sudden cardiac arrest;
initiating, with the one or more devices of the patient, a request to facilitate delivery of care that is to be provided by one or more care providers or bystanders for medical services to the patient in response to the determination that the implantable cardiac monitoring device has determined that the patient is experiencing the sudden cardiac arrest;

subsequent to initiating the request, confirming, with the one or more devices of the patient, that the patient is not experiencing the sudden cardiac arrest based at least in part on a second communication received from the implantable cardiac monitoring device, wherein the second communication received from the implantable cardiac monitoring device is different than the first communication, and wherein the second communication received from the implantable cardiac monitoring device includes at least one of: (1) information from the implantable cardiac monitoring device indicating that the patient is not experiencing the sudden cardiac arrest, or (2) data sensed by the implantable cardiac monitoring device from which the one or more devices can confirm that the patient is not experiencing the sudden cardiac arrest; and in response to the confirmation, outputting, with the one or more devices, information to cause a change in the request for the medical services to one or more of the same one or more care providers or bystanders.

20. The method of claim 19, wherein the request to facilitate delivery of care comprises a higher-level priority request, and wherein outputting the information to cause the change in the request for the medical services comprises outputting instructions to cease the output of the higher-level priority request and output a lower-level priority request, wherein the lower-level priority request requires fewer medical services as compared to the higher-level priority request.

21. The method of claim 19, wherein outputting the information to cause the change in the request for the medical services comprises causing the one or more devices to output information for an emergency response system of the one or more care providers indicating that the patient is not experiencing the sudden cardiac arrest.

22. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more physical states include one or more external physical states, and wherein the one or more external physical states comprise one or more of:

a posture of the patient;
an eye opening;
a face color;
facial tone; or
asymmetrical face or body response.

23. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more physical states include one or more internal physical states, and wherein the one or more internal physical states comprise one or more of:

an electrocardiogram;
an intracardiac or intrathoracic impedance;
a respiration rate;
a heart sound;
a pulse;
an oxygenation level;
change in blood volume;
a blood pressure;
change in cardiac rhythm;
change in cardiac rate; or
change in cardiac conduction pattern.

24. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more sensors comprise a camera of the one or more devices, wherein the sensed data comprises an image of a face of the patient captured with the camera, and wherein determining the one or more physical states of the patient based on sensed data from one or more sensors comprises at least one of determining whether one or both eyes of the patient are open based on the image of the face, or determining a color of the face of the patient.

25. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more sensors comprise at least one of an accelerometer or inertial measurement unit (IMU) of the one or more devices, wherein the sensed data comprises information indicative of a posture of the patient, and wherein determining the one or more physical states of the patient based on sensed data from one or more sensors comprises determining whether the patient is in a vertical posture based on the information indicative of the posture of the patient.

26. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more sensors comprise at least one of an accelerometer or inertial measurement unit (IMU) of the one or more devices, wherein the sensed data comprises information indicative of a time-series of positioning of the patient, and wherein determining the one or more physical states of the patient based on sensed data from one or more sensors comprises determining whether the patient fell based on the information indicative of the time-series of the positioning of the patient.

27. The method of claim 19, wherein confirming that the patient is not experiencing the sudden cardiac arrest comprises confirming that the patient is not experiencing the sudden cardiac arrest also based on one or more physical states of the patient, the method further comprising determining the one or more physical states of the patient based on sensed data from one or more sensors, wherein the one or more sensors comprises a microphone of the one or more devices, wherein the sensed data comprises information indicative of sound captured with the microphone, and wherein determining the one or more physical states of the patient based on sensed data from one or more sensors comprises determining whether the patient is in a physical state for providing sound based on the sound captured with the microphone.

28. The method of claim 19, wherein the data sensed by the implantable cardiac monitoring device from which the one or more devices can confirm that the patient is not experiencing the sudden cardiac arrest comprises data for at least one of a cardiac signal, a neurological signal, and a respiratory signal.

29. The method of claim 19, further comprising outputting, with the one or more devices, a request for patient feedback, wherein confirming that the patient is not experiencing the sudden cardiac arrest comprises confirming that the patient is not experiencing the sudden cardiac arrest also based on reception of the patient feedback responsive to the request for patient feedback.

30. The method of claim 19, wherein determining, based at least in part on the communication received from the implantable cardiac monitoring device, that the implantable cardiac monitoring device has determined that the patient is experiencing the sudden cardiac arrest comprises determining, in a first instance, that the implantable cardiac monitoring device has determined that the patient is experiencing the acute health event sudden cardiac arrest, the method further comprising:
- determining, in a second instance, based at least in part on a third communication received from the implantable cardiac monitoring device, that the implantable cardiac monitoring device has determined that the patient is experiencing the sudden cardiac arrest;
- determining, in the second instance, that medical services are being provided to the patient; and
- at least one of ceasing, preventing, or delaying output of an alert.

31. The method of claim 19, wherein at least one of the one or more devices of the patient comprises at least one of a smartphone, a smartwatch, a wearable ring, wearable health sensor, smart clothing, or an Internet of Things (IoT) device, and the sudden cardiac arrest is a sudden cardiac arrest (SCA).

32. One or more non-transitory computer-readable storage mediums storing instructions thereon that when executed cause one or more processors to:
- receive, from an implantable cardiac monitoring device, a first communication that indicates that a patient is experiencing a sudden cardiac arrest based on a determination by the implantable cardiac monitoring device that the patient is experiencing the sudden cardiac arrest based on sensing by the implantable cardiac monitoring device within the patient;
- determine, based at least in part on the first communication received from the implantable cardiac monitoring device, that the implantable cardiac monitoring device has determined that the patient is experiencing the sudden cardiac arrest;
- initiate a request to facilitate delivery of care that is to be provided by one or more care providers or bystanders for medical services to the patient in response to the determination that the implantable cardiac monitoring device has determined that the patient is experiencing the sudden cardiac arrest;
- subsequent to initiating the request, confirm that the patient is not experiencing the sudden cardiac arrest based at least in part on a second communication received from the implantable cardiac monitoring device, wherein the second communication received from the implantable cardiac monitoring device is different than the first communication, and wherein the second communication received from the implantable cardiac monitoring device includes at least one of: (1) information from the implantable cardiac monitoring device indicating that the patient is not experiencing the sudden cardiac arrest, or (2) data sensed by the implantable cardiac monitoring device from which the one or more processors can confirm that the patient is not experiencing the sudden cardiac arrest; and
- in response to the confirmation, output information to cause a change in the request for the medical services to one or more of the same one or more care providers or bystanders.

33. A system comprising:
- an implantable cardiac monitoring device configured to:
  - determine that a patient is experiencing a sudden cardiac arrest based on sensing by the implantable cardiac monitoring device within the patient; and
  - transmit a first communication that indicates that the patient is experiencing the sudden cardiac arrest; and
- one or more devices of the patient that are different than the implantable cardiac monitoring device, the one or more devices comprising processing circuitry configured to:
  - determine, based at least in part on the first communication received from the implantable cardiac monitoring device, that the implantable cardiac monitoring device has determined that the patient is experiencing the sudden cardiac arrest; and
  - initiate a request to facilitate delivery of care that is to be provided by one or more care providers or bystanders for medical services to the patient in response to the determination that the implantable cardiac monitoring device has determined that the patient is experiencing the sudden cardiac arrest;
- means for confirming, subsequent to initiating the request, that the patient is not experiencing the sudden cardiac arrest based at least in part on a second communication received from the implantable cardiac monitoring device, wherein the second communication received from the implantable cardiac monitoring device is different than the first communication, and wherein the second communication received from the implantable cardiac monitoring device includes at least one of: (1) information from the implantable cardiac monitoring device indicating that the patient is not experiencing the sudden cardiac arrest, or (2) data sensed by the implantable cardiac monitoring device from which the means for confirming can confirm that the patient is not experiencing the sudden cardiac arrest; and
- an output device configured to, in response to the confirmation, output information to cause a change in the request for the medical services to one or more of the same one or more care providers or bystanders.

* * * * *